United States Patent
Segawa et al.

(10) Patent No.: US 7,892,164 B2
(45) Date of Patent: Feb. 22, 2011

(54) CAPSULE MEDICAL APPARATUS

(75) Inventors: Hidetake Segawa, Hachioji (JP);
Takeshi Yokoi, Hino (JP); Wataru Ohno, Hachioji (JP)

(73) Assignee: Olympus Corporation, Tokyo (JP)

( * ) Notice: Subject to any disclaimer, the term of this patent is extended or adjusted under 35 U.S.C. 154(b) by 616 days.

(21) Appl. No.: 11/800,580

(22) Filed: May 7, 2007

(65) Prior Publication Data
US 2007/0219435 A1    Sep. 20, 2007

Related U.S. Application Data

(62) Division of application No. 10/634,044, filed on Aug. 4, 2003, now Pat. No. 7,473,218.

(30) Foreign Application Priority Data

| Aug. 6, 2002 | (JP) | 2002-229056 |
| Aug. 6, 2002 | (JP) | 2002-229057 |
| Feb. 18, 2003 | (JP) | 2003-039994 |

(51) Int. Cl.
*A61B 1/04* (2006.01)
(52) U.S. Cl. .......................... 600/109; 600/160; 348/76
(58) Field of Classification Search ................. 600/109, 600/160; 348/65, 76
See application file for complete search history.

(56) References Cited

U.S. PATENT DOCUMENTS

| 2,832,013 | A | * | 4/1958 | Pedersen et al. | 361/758 |
| 4,373,259 | A | * | 2/1983 | Motsch | 29/840 |
| 5,400,072 | A | | 3/1995 | Izumi et al. | |
| 5,854,507 | A | * | 12/1998 | Miremadi et al. | 257/686 |
| 5,914,534 | A | * | 6/1999 | Todd et al. | 257/773 |
| 5,986,693 | A | * | 11/1999 | Adair et al. | 348/76 |
| 6,490,168 | B1 | * | 12/2002 | Rochowicz et al. | 361/784 |
| 6,504,244 | B2 | * | 1/2003 | Ichinose et al. | 257/723 |
| 6,918,872 | B2 | * | 7/2005 | Yokoi et al. | 600/129 |
| 6,984,205 | B2 | * | 1/2006 | Gazdzinski | 600/160 |
| 7,039,453 | B2 | * | 5/2006 | Mullick et al. | 600/476 |
| 2002/0103417 | A1 | * | 8/2002 | Gazdzinski | 600/109 |

(Continued)

FOREIGN PATENT DOCUMENTS

JP    5-92003    4/1993

(Continued)

*Primary Examiner*—John P Leubecker
(74) *Attorney, Agent, or Firm*—Scully, Scott, Murphy & Presser, P.C.

(57) ABSTRACT

A capsule medical apparatus including: a cylindrical capsule-shaped exterior casing; a plurality of electrical substrates stored in the exterior casing; a connecting member using a plurality of soldering balls or a plurality of pins, the connecting member being electrically conductive and mechanically fixing the electrical substrates adjacent and opposed to one another, in a state where each of the plurality of electrical substrates are arranged in a direction orthogonal to a longitudinal direction of the exterior casing such that the electrical substrates are substantially parallel to one another; a battery; and a flexible substrate which is provided with a power pattern which is electrically conductive with the battery and transmits power by the battery, and on which the power pattern is connected so as to be electrically conductive at end surfaces of the plurality of electrical substrates opposed to one another in the longitudinal direction of the exterior casing.

14 Claims, 21 Drawing Sheets

U.S. PATENT DOCUMENTS

| | | | |
|---|---|---|---|
| 2003/0171649 A1* | 9/2003 | Yokoi et al. | 600/109 |
| 2004/0171914 A1* | 9/2004 | Avni | 600/160 |
| 2005/0288557 A1* | 12/2005 | Yokoi et al. | 600/176 |
| 2007/0135680 A1* | 6/2007 | Mizuno | 600/118 |
| 2007/0142710 A1* | 6/2007 | Yokoi et al. | 600/173 |

FOREIGN PATENT DOCUMENTS

| | | |
|---|---|---|
| JP | 7-153903 | 6/1995 |
| JP | 4-314417 | 11/1995 |
| JP | 2001-95756 | 4/2001 |
| JP | 2001-170002 | 6/2001 |
| WO | WO 02/102224 A2 | 12/2002 |

* cited by examiner

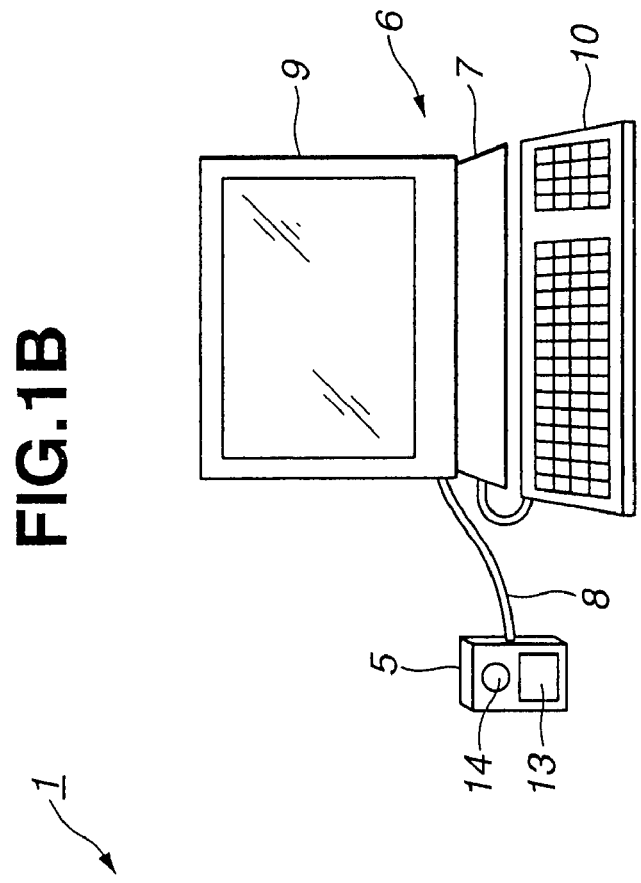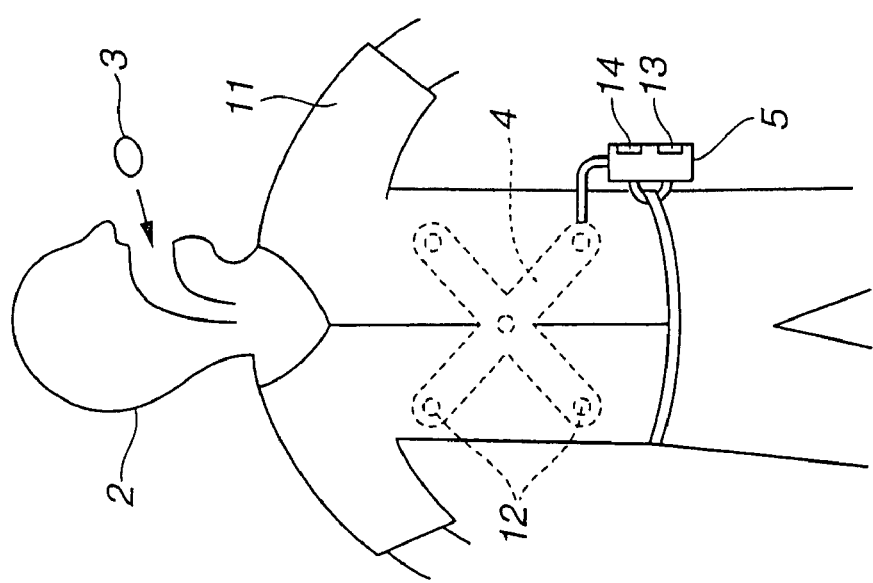

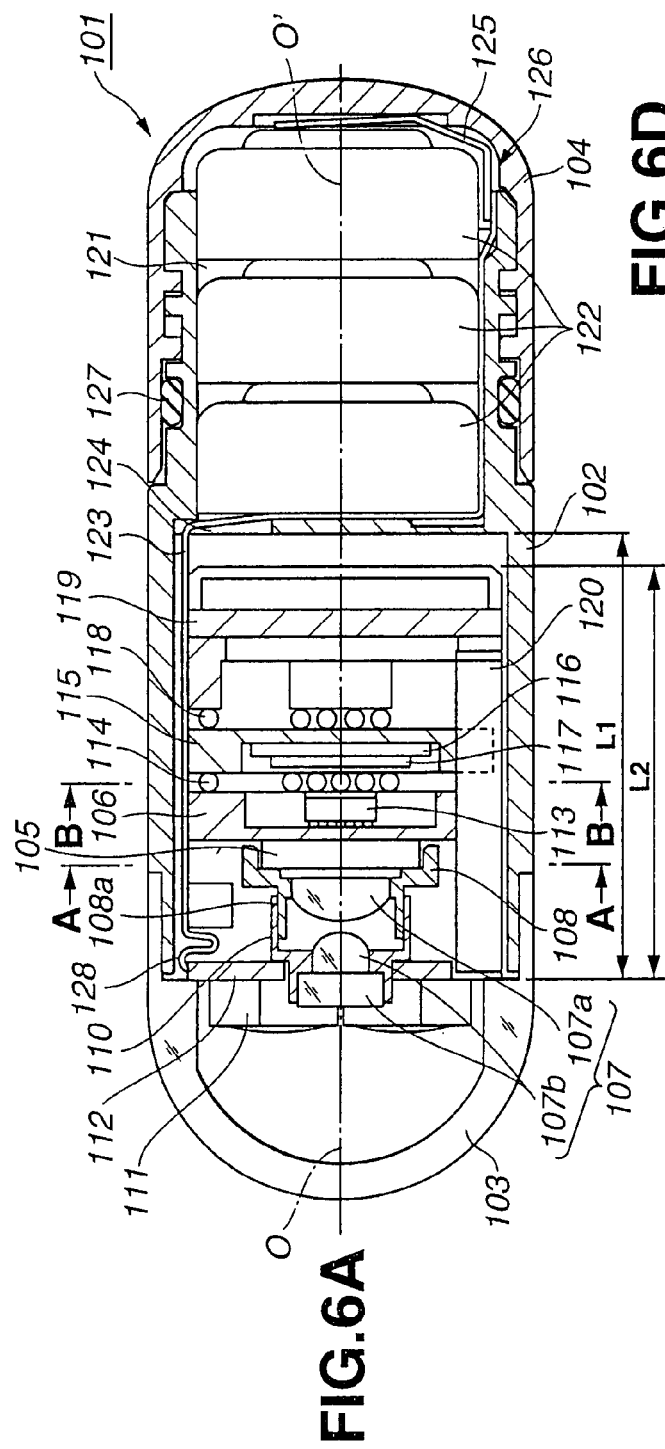
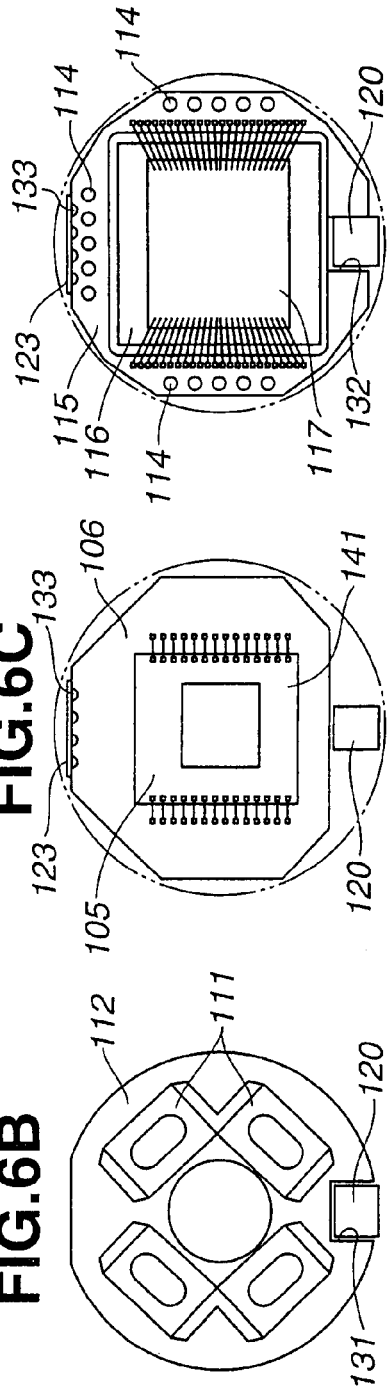

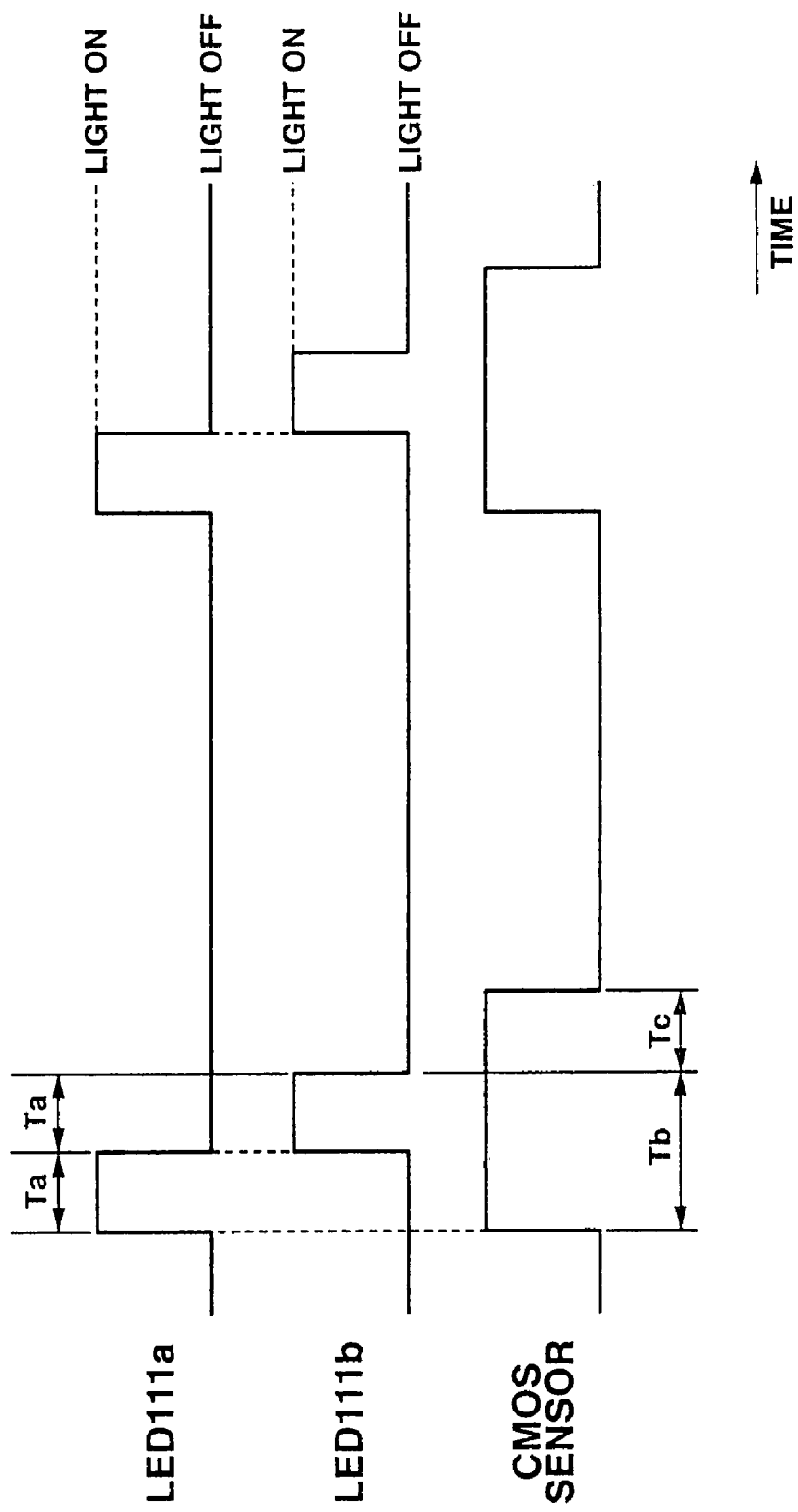

116 : FC, 117 : WB

116 : FC, 117 : FC

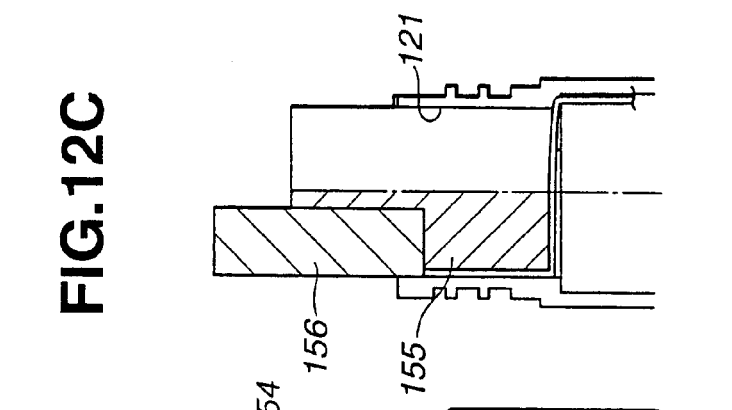
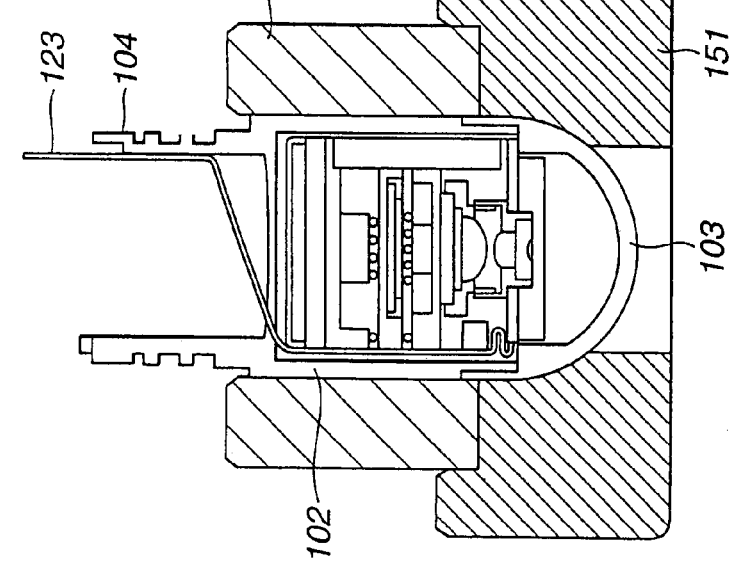
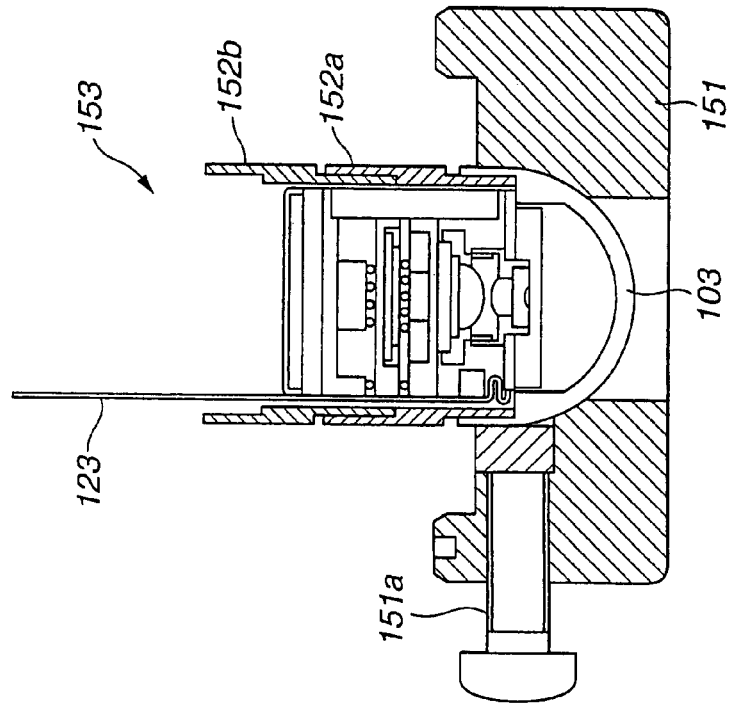

D1 > D2 > D12

FIG.29A FIG.29B
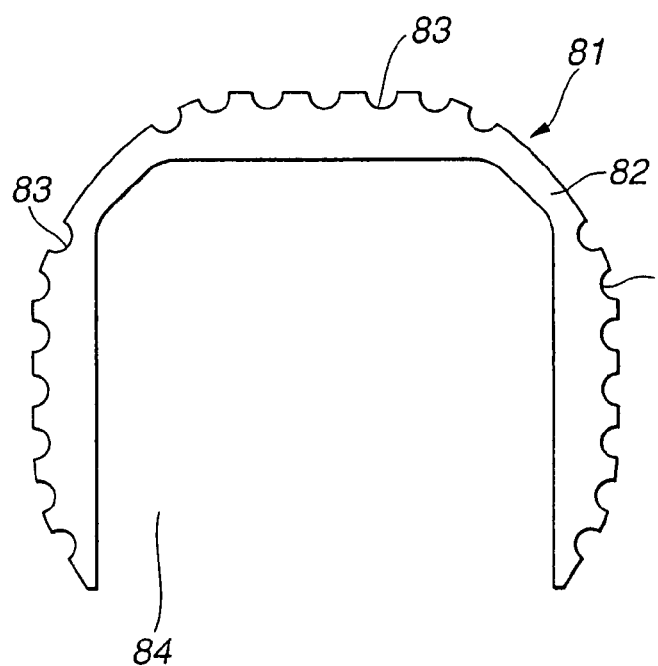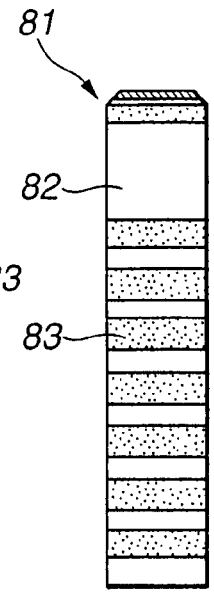
FIG.30
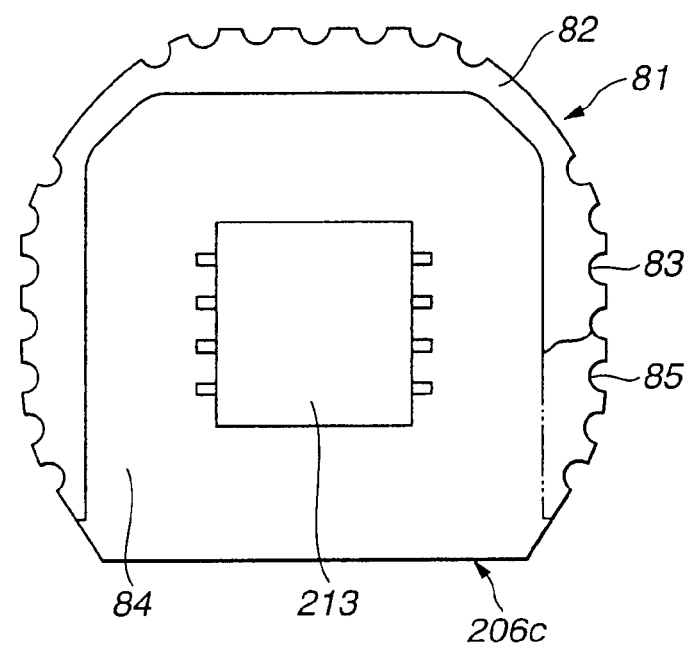

CAPSULE MEDICAL APPARATUS

This application is a divisional application of U.S. application Ser. No. 10/634,044 filed on Aug. 4, 2003, now U.S. Pat. No. 7,473,218 issued on Jan. 6, 2009, which claims benefit of Japanese Application Nos. 2002-229056 filed on Aug. 6, 2002, 2002-229057 filed on Aug. 6, 2002, and 2003-39994 filed on Feb. 18, 2003, the contents of each of which are incorporated by reference.

BACKGROUND OF THE INVENTION

1. Field of the Invention

The present invention relates to a capsule medical apparatus for examining the living body and an assembling method of the capsule medical apparatus.

2. Description of the Related Art

Japanese Unexamined Patent Application Publication Nos. 2001-95756 and 2001-333332 disclose swallow-type capsule endoscopes as first and second related arts.

In the first related art as disclosed in Japanese Unexamined Patent Application Publication No. 2001-95756, an image sensor 111 is fixed on the surface of a circular circuit board (1) 110 on which an image sensor window 112 is formed. An electric component holding casing 13 contains the image sensor window 112, the circular circuit board (1) 110, and the image sensor 111 together with another circuit board. An objective lens barrel 20 is held to an objective lens holding casing 12 which is formed integrally with the electric component holding casing 13 on the distal end side thereof.

In the second related art as disclosed in Japanese Unexamined Patent Application Publication No. 2001-333332, a barrel 1 comprises an attached portion of a lens 2 and an attached portion 14 formed to surround the circumference of an integrated circuit 4, as a solid-image pick-up device, or the integrated circuit 4 including the solid-image pick-up device. The barrel 1 is attached on the top surface of the integrated circuit 4 to be modified in the optical axis. A stud bump 40 is formed on the top surface of the integrated circuit 4. A terminal portion 51 for mounting is continuously connected to an external electric connecting terminal 52 by applying pressure at the position corresponding to the stud bump 40 of the barrel 1.

U.S. Pat. No. 5,400,072 discloses a video camera unit having a focusing adjusting function with small size.

SUMMARY OF THE INVENTION

Accordingly, there is provided an assembling method of a capsule medical apparatus including a sealed capsule having an illuminating unit, an image pick-up unit for picking up an image of a portion illuminated by the illuminating unit, and an objective optical system in front of the image pick-up unit. The assembling method comprises: a positioning step of positioning a relative position of a reference position of a fixing frame of the objective optical system so that it matches a reference position of an image area of the image pick-up unit; and a fixing step of, after the positioning step, fixing the image pick-up unit and the fixing frame so that a reference down-surface of the fixing frame comes into contact with a top surface of the image pick-up unit.

BRIEF DESCRIPTION OF THE DRAWINGS

FIGS. 1A to 5B are diagrams according to a first embodiment of the present invention, FIG. 1A is a diagram showing a capsule endoscope system according to the first embodiment;

FIG. 1B is a diagram showing a recording and display device;

FIG. 2 is a longitudinal cross-sectional view showing the structure of a capsule endoscope;

FIG. 4 is an explanatory diagram showing another positioning method;

FIGS. 5A and 5B are a front view and a cross-sectional view showing the structure of a fixing frame which is positioned to the sensor substrate and, thereafter, is fixed for watertightness;

FIGS. 6A to 14 are diagrams according to a second embodiment of the present invention, FIG. 6A is a longitudinal cross-sectional view showing a capsule endoscope according to the second embodiment;

FIG. 6B is a front view of an LED substrate shown in FIG. 6A in the optical axis direction;

FIGS. 6C and 6D are A-A and B-B cross-sectional views in FIG. 6A;

FIG. 6E is a timing chart for explaining the operation for intermittently lighting on two sets of LEDs;

FIG. 7 is a cross-sectional view showing the structure on the distal end side according to a modification of the second embodiment;

FIG. 8 is a diagram showing the structure of a power line using a flexible substrate;

FIGS. 12A to 12C are explanatory diagrams showing the processing routine for assembling the distal end cover and an image pick-up unit;

FIG. 14 is a diagram showing a state for changing the thickness of the distal end cover outside of a field-of-view angle;

FIGS. 16 to 19 are diagrams according to a fourth embodiment,

FIG. 16 is a cross-sectional view showing the internal structure of a capsule medical apparatus according to the fourth embodiment;

FIG. 18 is a diagram showing a state when two electric substrates are positioned and are temporarily fixed by using a fixing jig;

FIG. 19 is a diagram schematically showing temperature characteristics of heating processing upon soldering by using a reflow furnace;

FIGS. 20 to 24 are diagrams according to a fifth embodiment of the present invention, FIG. 20 is a diagram showing an example of the structure for assembling substrates according to the fifth embodiment;

FIG. 23 is a side view showing an example of the structure for assembling the substrates according to a third modification;

FIG. 24 is a diagram showing an example of the structure for assembling the substrates according to a fourth modification;

FIGS. 25 to 28B are diagrams according to a sixth embodiment of the present invention, FIG. 25 is a side view showing an example of the structure for assembling substrates according to the sixth embodiment;

FIG. 26 is a side view showing an example of the structure for assembling the substrates according to a first modification of the sixth embodiment;

FIG. 28B is a diagram showing another example of the structure for assembling the substrates by processing the lead frame;

FIGS. 29A to 31 are diagrams according to a seventh embodiment of the present invention, FIGS. 29A and 29B are a plan view and a right-side view showing a connecting member of a substrate according to the seventh embodiment;

FIG. 30 is a plan view showing a state in which one substrate is overlapped to the connecting member; and FIG. 31 is a longitudinal cross-sectional view showing the inner structure of a capsule medical apparatus according to a modification.

DESCRIPTION OF THE PREFERRED EMBODIMENTS

Figure 2:
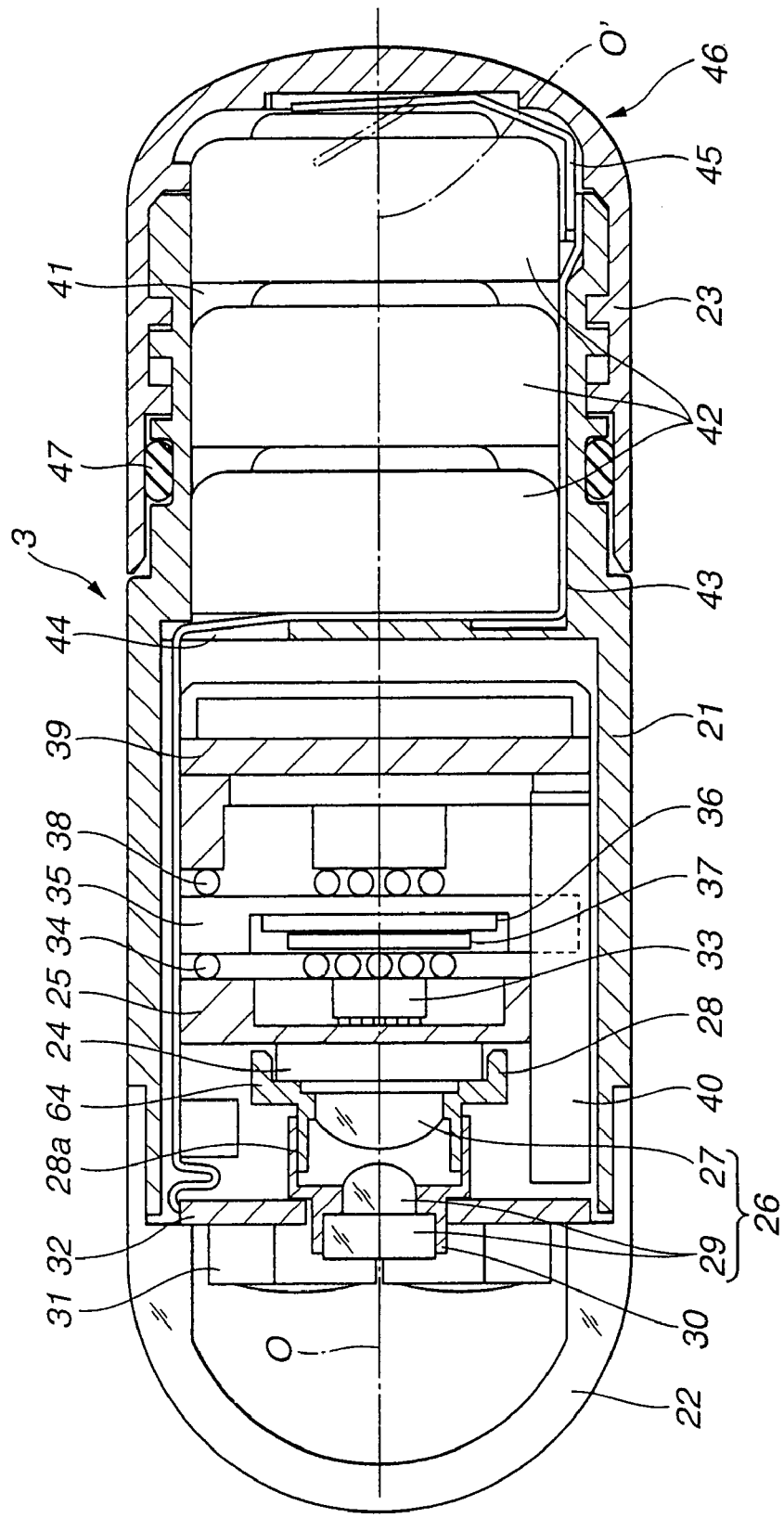

Hereinbelow, a description is given of embodiments of the present invention with reference to the drawings.

First Embodiment

A first embodiment of the present invention will be described with reference to FIGS. 1A to 5B.

Referring to FIG. 1A, a capsule endoscope system 1 according to the first embodiment of the present invention comprises: a capsule endoscope 3 which transmits by radio an image signal for optically picking up an inner-wall surface of the luminal portion in the coelom, upon passing though the luminal portion in the coelom by being swallowed from the mouth of a patient 2; and an extracorporeal unit 5 (arranged to the outside of the patient 2) having functions for receiving the signal transmitted by the capsule endoscope 3 by an antenna unit 4 arranged to the outside of the patient 2 and for storing the image and for displaying the image.

The extracorporeal unit 5 incorporates a hard disk with the size of a compact flash (R) having a capacity of 1 GB so as to store the image data.

The image data stored in the extracorporeal unit 5 is displayed as an image by connecting the capsule endoscope system 1 to a recording and display device 7 shown in FIG. 1B during examination or after ending the examination.

Referring to FIG. 1B, the extracorporeal unit 5 is detachably connected to a personal computer (hereinafter, abbreviated to a PC) 7 comprising a recording and display device 6 by a communication cable for communication such as a USB cable 8.

The PC 7 captures the image stored in the extracorporeal unit 5, the captured image is stored in the hard disk, it is processed for display operation, and the stored image is displayed by a display unit (monitoring unit) 9 of the PC 7. A key board 10 as an operating board for data input operation is connected to the PC 7.

The USB cable 8 may be any of the USB 1.0, USB 1.1, and USB 2 standards. The data is serially communicated by the RS-232C or IEEE 1394 standard. The present invention is not limited to the serial data communication and may use parallel data communication.

Referring to FIG. 1A, upon examination using the endoscope by swallowing the capsule 3, an antenna unit 4 having a plurality of antennas 12 is attached to the inside of a shield shirt 11 having a shielding function, worn by the patient 2. The image is picked up by the capsule 3, the signal transmitted from the incorporated antenna is received, and the picked-up image is stored in the extracorporeal unit 5 connected to the antenna unit 4. The extracorporeal unit 5 is attached to, for example, a belt of the patient 2 by a detachable hook.

The extracorporeal unit 5 is, for example, box-shaped. Further, the extracorporeal unit 5 comprises: a liquid crystal monitor 13 as a display device for displaying an image, in front thereof; and an operating button 14 for control operation. The extracorporeal unit 5 comprises a receiving and transmitting circuit (communication circuit), a control circuit, an image data display circuit, and a power supply, therein.

FIG. 2 shows the specific structure of the capsule endoscope 3.

In the capsule endoscope 3, a distal end cover 22 which is formed by hemispherically shaping a transparent soft member is watertightly fixed to the front end of a cylindrical capsule main body (hereinafter, referred to as a main body) 21, and a detachable rear cover 23 is watertightly attached at the rear end of the main body 21. Further, the distal end cover 22, the main body 21, and the rear cover 23 watertightly cover and incorporate image pick-up means and power supply means.

That is, a CMOS module is formed by attaching a CMOS sensor 24 as the image pick-up means to a sensor substrate 25 in the center thereof, facing the distal end cover 22. A fixing frame 28 has a fixing-side lens 27 (positioned most adjacently to the CMOS sensor 24) of an objective lens system 26, and it is positioned and fixed to an image area (image pick-up area) side of the CMOS sensor 24, as will be described later.

A movable frame 30 having a movable-side lens 29 of the objective lens system 26 is fit into a cylindrical portion 28a in the fixing frame 28, and it is movable in the optical axis direction of the objective lens system 26. That is, the cylindrical portion 28a is a guide of the movable frame 30. The movable 30 advances and returns in the optical axis direction for the adjustment of focusing and, after that, it is fixed.

The objective lens system 26 after adjusting the focusing forms on an image pick-up surface (image area) of the CMOS sensor 24, a subject image of the luminal portion in the coelom in a focusing state.

A white LED 31 as illuminating means is mounted on an LED substrate 32. The LED substrate 32 is fixed to the cylindrical portion of the movable frame 30 by being fit into a hole portion arranged in the center thereof. Thus, e.g., four LEDs 31 on the circumference of an image pick-up range of the objective lens system 26 illuminate the image pick-up range with substantial uniformity.

A cave portion is formed on the rear surface of the sensor substrate 25. An IC chip 33 is flip-mounted on the cave portion. The rear surface side of the sensor substrate 25 is connected to an image pick-up processing and control substrate 35 for driving the CMOS sensor 24 via a connecting terminal 34 by using soldering balls and for performing signal processing and controlling the image picked-up output signal.

A cave portion is formed on the front surface side of the image pick-up processing and control substrate 35. A first IC chip 36 is flip-mounted on the cave portion. Further, a second IC chip 37 is mounted on the top surface of the IC chip 36 by wire bonding.

The rear surface side of the image pick-up processing and control substrate 35 is connected to a communication substrate 39 via a connecting terminal 38 by the soldering balls. Electric parts are mounted to both surfaces of the communication substrate 39, and a Bluetooth-type radio communication module is formed.

As mentioned above, the sensor substrate 25, the image pick-up processing and control substrate 35, and the communication substrate 39 are laminated at an interval between the connecting terminals 34 and 38 in the axial direction of the main body 21, thereby forming the circuit structure for mounting the electric parts with high density.

A part of the side surfaces of the sensor substrate 25 and the image pick-up processing and control substrate 35 are notched. The antenna 40 connected to the communication substrate 39 is arranged along the notch portion.

The image signal photoelectrically converted by the CMOS sensor 24 is transmitted to the extracorporeal unit 5 via the communication substrate 39, an instruction signal from the extracorporeal unit 5 is received, and the period for illumination and the image pick-up operation are changed.

A battery accommodating chamber 41 is formed on the back surface of the communication substrate 39 and the battery accommodating chamber 41 accommodates, e.g., three batteries 42.

A flexible substrate 43 is arranged along the inner surface of the main body 21 opposed to the antenna 40. The front end of the flexible substrate 43 is connected to the LED substrate 32, is bent at an angle of approximately 90° by an opening portion 44 arranged on the rear surface side of the communication substrate 39, is inserted in a battery accommodating chamber 41, and comes into contact with the positive of the battery 42 in the halfway thereof (a conductive pattern is exposed in a portion contact with the positive of the battery 42).

The flexible substrate 43 is bent above, is made conductive to the positive of the battery 42 in the halfway thereof, is bent at the angle of 90° along the side surface of the battery accommodating chamber 41 on the antenna 40 side, and is extended backward.

The rear end of the flexible substrate 43 may be changed from a non-connecting state to a connecting state, or from the connecting state to the non-connecting state, with regard to the end portion on the side surface of the a plate spring 45 held to the inner surface of the cave portion of the rear cover 23 by rotation of the rear cover 23. Thus, a power switch 46 is formed to turn off to on, or on to off the power of the battery 42.

The plate spring 45 is L-shaped, approximately U-shaped. The center portion of the plate spring 45 is held to the rear cover 23. Both ends of the plate spring 45 are elastically modified and one end comes into contact with the negative of the battery 42 accommodated in the battery accommodating chamber 41.

The rear cover 23 is moved to the main body 21 side, is rotated at a predetermined angle, is moved in the direction apart from the main body 21, is rotated at a predetermined angle, and is pressed toward the main body 21 side. Referring to FIG. 2, the front end portion of the plate spring 45 comes into contact with an exposing pattern portion at the rear end of the flexible substrate 43 and, thus, the power of the batteries 42 is supplied to the communication substrate 39, the image pick-up processing and control substrate 35, the sensor substrate 25, and the LED substrate 32 via the power pattern of the flexible substrate 45.

The shape of the plate spring 45 when the batteries 42 are not accommodated are shown by a two-dot-dashed line of the plate spring 45 in FIG. 2. The batteries 42 are accommodated and then the plate spring 45 comes into contact with the negative of the batteries 42.

An O-shaped ring 47 for watertightness is inserted between the outer-circumferential surface of the main body 21 and the inner-circumferential surface of the rear cover 23.

A bending portion (play portion) is formed near the front end of the flexible substrate 43 and it is connected to the LED substrate 32, thereby adjusting the focusing.

As will be described hereinafter with reference to FIG. 4, the center position of an image area 61 in the CMOS sensor 24 is positioned and fixed to the center position of the fixing frame 28. After that, the movable frame 30 is adjusted for the focusing and is fixed to the fixing frame 28. Further, an image pick-up unit to which the LED substrate 32 is fixed is positioned at the position where a step surface of the distal end cover 22 is abutted on the end surface of the LED substrate 32. An assembling jig (not shown) positions the positioning operation in the circumferential direction caused by the positioning operation of the image pick-up unit. Thus, the pupil position of the objective lens system 26 is fixed at the center position of the radius of a hemispherical surface of the distal end cover 22.

Further, the main body 21 is positioned and fixed, via the jig, to the distal end cover 22 to which the image pick-up unit is attached. As a result of the positioning operation of the main body 21, the optical axis O of the objective lens system 26 is set to match the central axis O' of the main body 21 as shown in FIG. 2.

In the capsule endoscope 3 with the above-mentioned structure, a center 61a of the image area 61 in the CMOS sensor 24 is fixed to be on the optical axis O of the objective lens system 26. Further, the center 61a of the image area 61 is positioned to be on the central axis of the cylindrical casing of the main body 21.

That is, according to the first embodiment, the image pick-up means having the single optical characteristic and a sufficiently suppressed deviation-angle is positioned and is incorporated in the capsule. If the same type of the capsule sensor 3 is not used, the image of the CMOS sensor 24 is displayed on the display portion 9 and then the picked-up images have the same quality by setting the individual capsule endoscopes 3.

Upon displaying the picked-up image on the display means, the picked-up images displayed thereon are substantially the same although having slight differences. That is, since there is no variation in angle of deviation, the picked-up images have the same quality by setting the pick-up states of the capsule endoscopes 3. The deviated and varied image range is solved upon varying the angles of deviation.

When the capsule endoscope 3 is rotated in the coelom, the picked-up image is substantially overlapped to the image by simply rotating the image therebefore in the center (if the image area is not circular, the above description is not applied on the circumferential side).

On the other hand, in the related arts, the variation in optical characteristics causes the image obtained by rotation around the center deviated from the center thereof as a result of rotation. Further, the deviated positions are varied and therefore the difference is caused in the picked-up images (that is, according to the related arts, the image pick-up system has the optical characteristics with the angles of deviation and the varied (different) images are obtained even in the same image pick-up state).

Figure 3A:
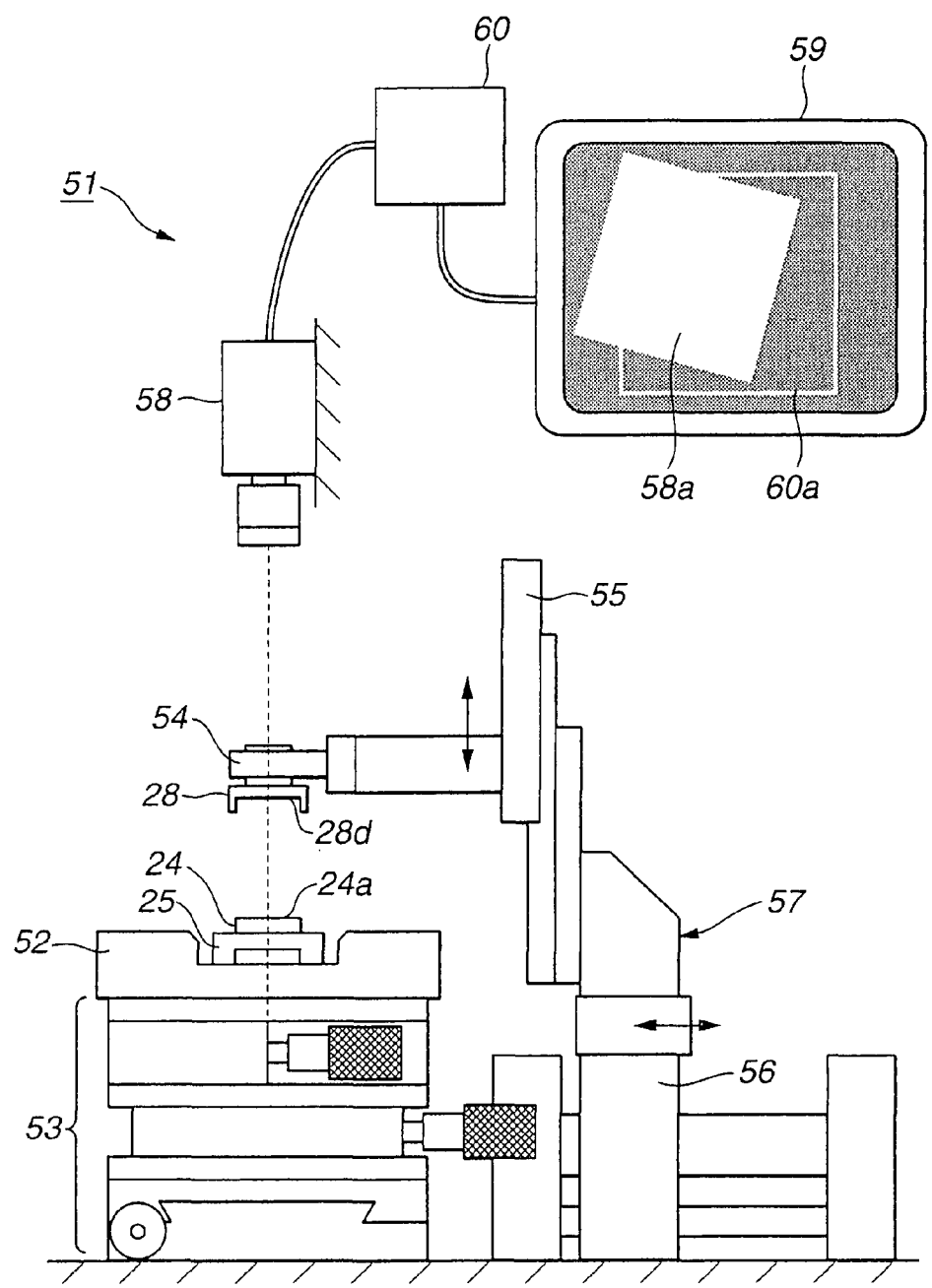
FIG. 3A is a diagram showing a state for positioning a fixing frame to a sensor substrate on which an image pick-up sensor is mounted by using an assembling jig.
Figure 3B:
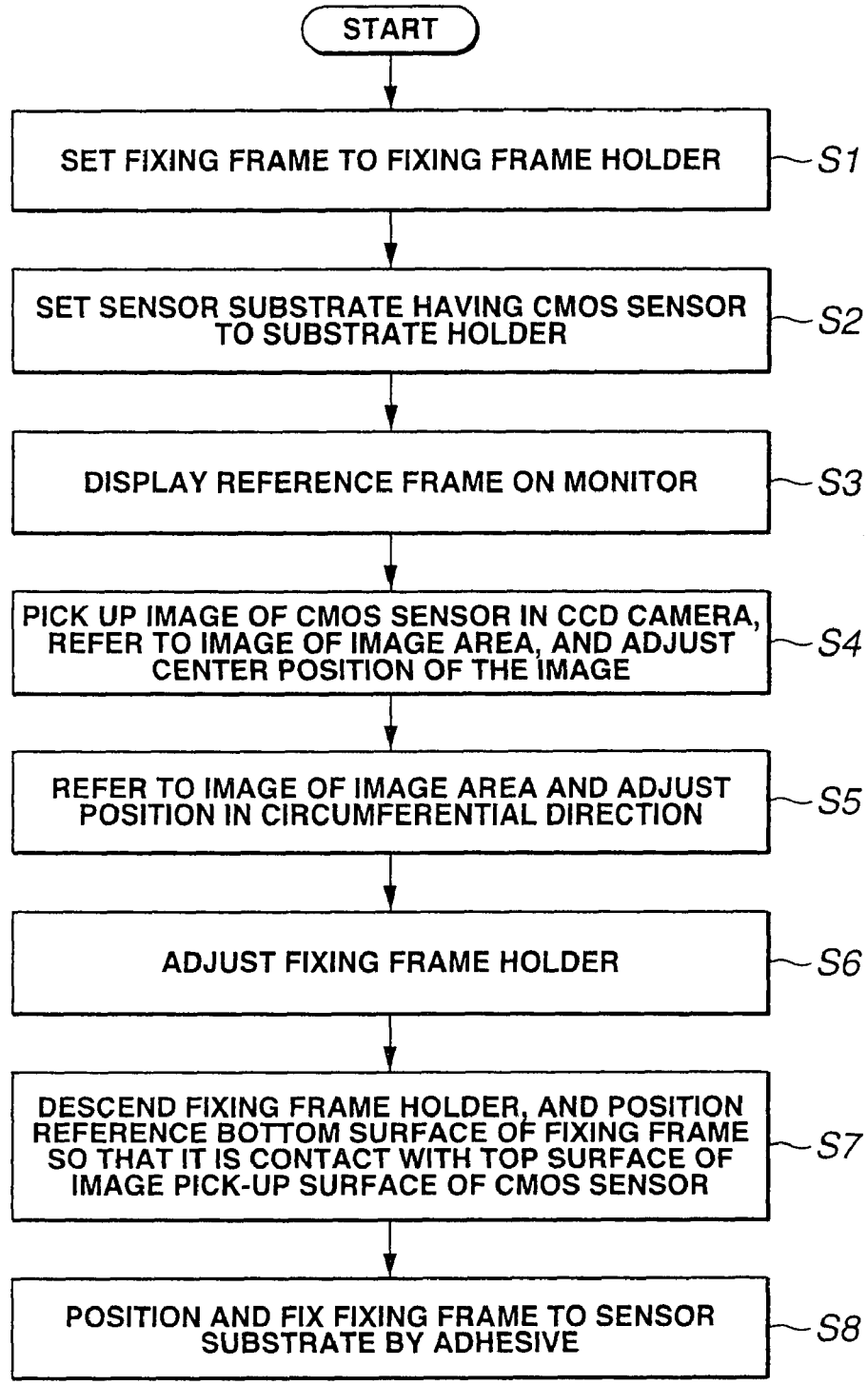
FIG. 3B is a flow diagram showing a procedure for positioning and fixing the fixing frame having an objective optical system mounted on the sensor substrate using the assembling jig shown in FIG. 3A.

Next, a description is given of an assembling method for positioning to the sensor substrate 25 having the CMOS sensor 24, the fixing frame 28 to which the optical member nearest to the image pick-up means of the objective lens system 26 is fixed with reference to FIGS. 3A and 3B.

According to the assembling method, it is possible to provide the capsule endoscope 3 having the image pick-up optical system having precisely assembled optical system and image pick-up means whose image is formed by the optical system, through positioning processing and fixing processing for fixing with an adhesive after the positioning processing.

Referring to FIG. 3A, an assembling jig 51 comprises: a substrate holder 52 which positions and holds the sensor substrate 25; an XYθ stage 53 which movably holds the substrate holder 52 in the X and Y directions as orthogonal directions of horizontal planes and which can hold it at an arbitrary angle θ around the center position; a fixing frame holder 54 which holds the fixing frame 28; a Z-axis stage 55 which holds, upstream, the fixing frame holder 54 movably in the Z-axis direction orthogonal to the horizontal planes; an assembling jig main body 57 having a slider 56 for freely moving the Z-axis stage 55 in a predetermined direction (e.g., X direction); a CCD camera 58 which is positioned and is held upstream of the substrate holder 52; a monitor 59 which displays an image 58a of the CCD camera 58; and a signal generating device 60 which generates a signal for displaying a reference frame 60a of the image area of the CMOS sensor 24 corresponding to a state in which the image is superimposed to the image 58a of the image area and is positioned on the monitor 59.

The assembling processing is performed by using the assembling jig 51 in accordance with the processing routine shown in FIG. 3B.

First, the assembling jig 51 is set so that the center of rotation of the XYθ stage 53 is positioned on the optical axis of the image pick-up system of the CCD camera 58. Further, the center of the fixing frame holder 54 for holding the fixing frame 28 is adjusted so that it is positioned on the optical axis of the CCD camera 58.

A reference frame 60a displayed on the display surface of the monitor 59 is adjusted so that the reference position of the reference frame 60a, e.g., the center position is in the center of the display surface. Upon displaying the image of the CCD camera 58 on the display surface of the monitor 59, the center position of the image is displayed in the center of the display surface.

Referring to FIG. 3B, in step S1, the fixing frame 28 is set to the fixing frame holder 54.

In this case, the fixing frame holder 54 to which the fixing frame 28 is set is moved to the outside of the field of view of the CCD camera 58. For example, the slider 56 is moved to the right and is slid to the outside of the field of view.

In step S2, the processing is performed to set the sensor substrate 25 on which the CMOS sensor 24 is attached to the substrate holder 52.

In step S3, the reference frame 60a is displayed on the display surface of the monitor 59. In this case, the reference frame 60a is displayed so that the center position of the display surface is in the center thereof.

In step S4, the CCD camera 58 picks up the image of the CMOS sensor 24 on the sensor substrate 25. In this case, the movement of the XYθ stage 53 is adjusted so that the center position of the image 58a of the image area in the CMOS sensor 24 is in the center of the display surface of the monitor 59.

As displayed on the monitor 59 shown in FIG. 3A, the movement of the XYθ stage 53 is not adjusted. After adjusting the movement of the XYθ stage 53, the center of the image 58a is set to match the center of the reference frame 60a.

In step S5, the size of the image 58a of the image area displayed on the display surface of the monitor 59 by changing a zooming ratio of the image pick-up system in the CCD camera 58 is adjusted to match the size of the reference frame 60a, and the image 58a is adjusted by rotating the XYθ stage 53 so that it is overlapped to the reference frame 60a.

The size of the image 58a of the image area is not necessarily adjusted to be overlapped to the size of the reference frame 60a. In this case, the size of the image 58a of the image area is used for the positioning operation in the circumferential direction. Therefore, if the positioning operation can be performed in the circumferential direction, the center of the image 58a may be set to match the center of the reference frame 60a. Further, if the fixing frame 28 has a rotationally symmetrical shape, the positioning operation in the circumferential direction is not necessary.

In place of changing the zooming ratio of the image pick-up system of the CCD camera 58, the size of the reference frame 60a may be changed on the signal processing device 60 side.

In step S6, the fixing frame holder 54 (outside the field of view of the CCD camera 58) is slid to the left, and the position of the fixing frame holder 54 is adjusted so that the center of the fixing frame holder 54 matches the center of the reference frame 60a.

In step S7, the fixing frame holder 54 is descended and a reference under-surface 28d as the reference of the fixing frame 28 is placed (positioned) and is contact with the upper surface of the CMOS sensor 24, namely, an image pick-up surface upper-surface 24a.

In step S8, an adhesive is coated by using a dispenser and is hardened. Thus, the fixing frame 28 is positioned and is fixed to the sensor substrate 25.

As mentioned above, the fixing frame 28 is fixed to the sensor 25. Therefore, the fixing frame 28 is precisely positioned and is fixed to the sensor substrate 25, and the optical system and the image pick-up means are assembled to the capsule endoscope 3 with high accuracy.

The assembling method using the manual assembling jig 51 is described as mentioned above. However, in the similar view, image recognizing means may be used, a recognizing result may be used, and a stage may automatically be moved and be adjusted.

The foregoing description is given of the assembling method using the reference frame 60a as the reference of the image area of the CMOS sensor 24. However, another reference position may be used as will be described hereinbelow.

Figure 4:
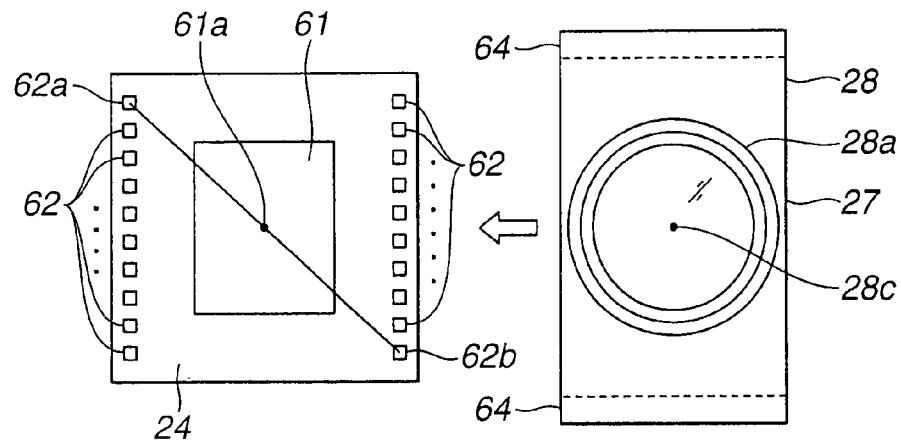

Referring to FIG. 4, the CMOS sensor 24 has an image area 61 in the center thereof. Bonding pads 62a and 62 (and 62 and 62b) are formed symmetrically on the right and left sides. In this case, the bonding pad 62 is not formed on the top and down sides.

The bonding pad 62a on the upper left and the bonding pad 62b on the down right are set as the reference positions. In this case, the center position of a line connecting the bonding pad 62a and the bonding pad 62b matches the position of the center 61a of the image area 61.

In this case, the sensor substrate 25, to which the CMOS sensor 24 shown in FIG. 4 is attached, is set to the substrate holder 52 of the assembling jig 51 shown in FIG. 3. The image of the CMOS sensor 24 is displayed on the monitor 59. Then, the center 61a of the image area 61 is displayed at the reference position such as the center position of the monitor 59.

Figure 5A:
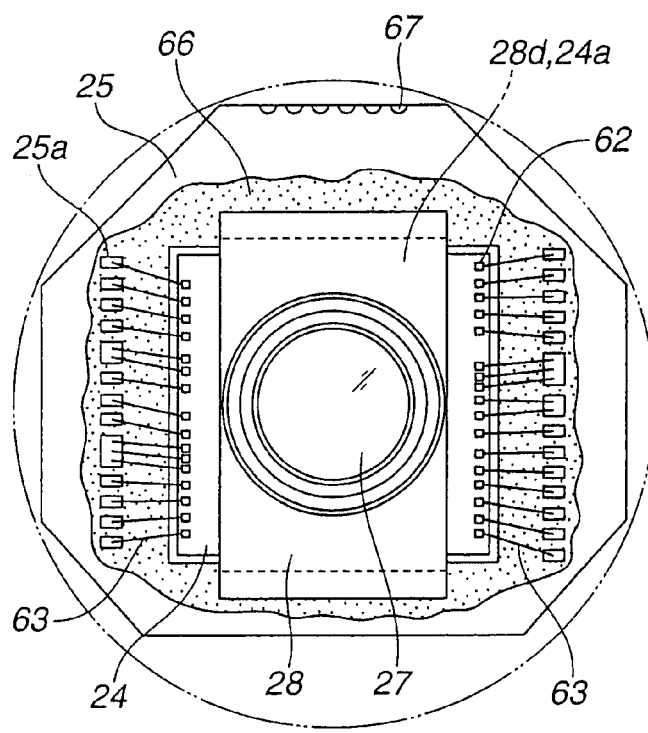
Figure 5B:
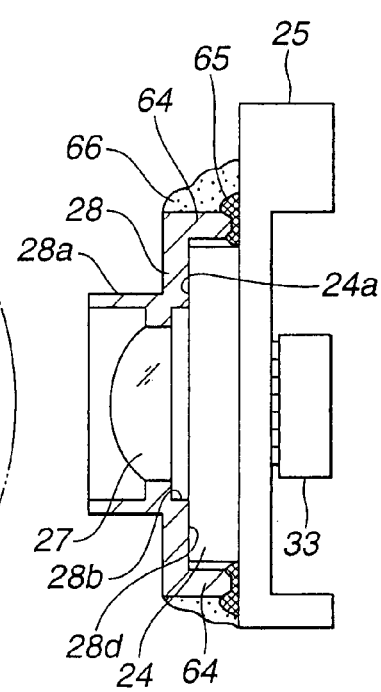

Referring to FIG. 5B, leg portions 64 are arranged on the side having no bonding pad 62 in the CMOS sensor 24 of the fixing frame 28, specifically, on the top and bottom sides. A cave portion interval between the leg portions 64 are set to have the size slightly larger than that of the CMOS sensor 24 in the top and bottom direction. When the fixing frame 28 is positioned to the CMOS sensor 24 side and the reference down-surface of the fixing frame 28 comes into contact with the image pick-up surface of the upper surface of the CMOS sensor 24, referring to FIGS. 5A and 5B, the leg portions 64 are extended to the side surfaces in the top and bottom direction of the CMOS sensor 24 (as will be described later, end portions of the leg portions 64 can easily and temporarily be stopped to the sensor substrate 25 by a temporary adhesive 65).

The image area 61 of the CMOS sensor 24 is displayed at the reference position on the monitor 59. After that, the fixing frame 28 shown in FIG. 4 is held by the fixing frame holder 54 and the image of the fixing frame 28 is displayed on the monitor 59. In this case, the image portion of the center 28c of the fixing frame 28 (to which the fixing-side lens 27 is attached) is set to be overlapped to the image portion of the center 61a of the image area 61. Further, the Z-axis stage 55 is descended and the fixing frame 28 is placed and is positioned on the CMOS sensor 24.

This case is shown in FIGS. 5A and 5B (incidentally, in a state before the fixing using the adhesives 65 and 66).

Upon the positioning operation as shown in FIG. 4, the fixing frame 28 has such a shape that a corner portion near the image area 61 or at least one part of circuits near the CMOS sensor 24 is viewed from the top.

FIGS. 5A and 5B show a state in which the fixing frame 28 positioned as shown in FIG. 3 or 4 is watertightly fixed to the sensor substrate 25 on which the CMOS sensor 24 is mounted. Incidentally, FIG. 5A shows a plan view and FIG. 5B shows a cross-sectional view of the side surface.

Referring to FIG. 5A, the bonding pad 62 of the CMOS sensor 24, which is attached to the sensor substrate 25, is connected to a pad 25a on the sensor substrate 25 side by a wire bonding 63.

As mentioned above, the fixing frame 28 has the leg portions 64 on the top and bottom sides thereof, and the leg portions 64 are extended to the side surfaces on the top and bottom of the CMOS sensor 24 and the end portions of the leg portions 64 are adjacent to the sensor substrate 25.

Referring to FIG. 5B, in the positioning state, the leg portions 64 are temporarily stopped to the sensor substrate 25 by using the temporary adhesive 65. After that, the circumference of the temporarily stopped portion is watertightly fixed by using the adhesive 66, including the wire bonding portion.

Referring to FIG. 5B, a notch portion 28b is formed to the fixing frame 28 so that a predetermined interval is formed between the portion for fixing the fixing-side lens 27 in the fixing frame 28 and the image area 61 of the CMOS sensor 24. As a result, when the image area 61 of the CMOS sensor 24 has a micro lens, the fixing frame 28 is attached without modifying the micro lens.

Referring to FIG. 5A, the sensor substrate 25 is approximately circular-shaped, e.g., is octagon-shaped. The top portion of the sensor substrate 25 has a connecting portion 67 which is connected to the pattern of the flexible substrate 45.

The fixing-side lens 27 and the fixing frame 28 having the fixing-side lens 27 are made of a material having the tolerance for the temperature for soldering of the sensor substrate 25. Specifically, the fixing frame 28 is made of a hard material such as stainless, ceramics, or heat-resisting resin. The fixing-side lens 27 is made of glass or heat-resisting resin.

The optical member such as the movable lens 29 is made of a material which resists heat of the soldering, similarly to the fixing-side lens 27. Further, the movable frame 30 is made of a material which resists heat of the soldering, similarly to the fixing frame 28.

As the reference position of the image pick-up means upon positioning the fixing frame 28, it is possible to use a peripheral circuit of the image pick-up means such as the bonding pad formed in the same processing as the formation of the corner portion near the image area 61 or the image area 61.

According to the first embodiment, the capsule endoscope 3 accommodates the batteries 42. However, the capsule endoscope 3 may incorporate power generating means in the capsule endoscope 3, e.g., a coil is incorporated in place of the batteries 42 and electric energy is induced by applying an AC magnetic field from the outside of the living body. Or, the battery may be charged by electric energy induced to the coil incorporated in the capsule endoscope 3 by using the AC magnetic field from the outside while the number of the included batteries 42 is reduced. Alternately, the power generation and the charging may be performed by supplying electro-magnetic waves.

In the capsule endoscope 3 with the above-mentioned structure, the sensor substrate 25 having the image pick-up sensor comprises the objective lens system 26, and the fixing frame 28, to which the fixing-side lens 27 nearest to the image pick-up sensor is attached, is positioned and is fixed to the sensor substrate 25. Thus, the capsule endoscope 3 is realized with the same optical characteristics and with the extremely reduced variation due to the individual difference.

According to the assembling method according to the first embodiment, the capsule endoscope 3 is produced with the same optical characteristic and with the extremely reduced variation due to the individual difference.

According to the first embodiment, in the capsule medical apparatus for medical actions such as examination, curing, and treatment in the body, a plurality of electric substrates having at least different functions are electrically conductive and are mechanically fixed via a connecting member to be roughly in parallel with each other in a capsule-shaped exterior portion. Further, the capsule medical apparatus comprises an electric circuit block having an outer shape slightly smaller than the inner diameter of the exterior portion. Consequently, the capsule medical apparatus is realized with the small size and preferable assembling performance, in which the plurality of electric substrate are connected in parallel with each other with high accuracy.

Next, a description is given of a capsule endoscope which is easily swallowed by arranging necessary functions with high density, and of an assembling method thereof.

Second Embodiment

Next, a description is given of a second embodiment of the present invention with reference to FIGS. 6A to 14.

Referring to FIG. 6A, a capsule endoscope 101 according to the second embodiment of the present invention comprises: a cylindrical-shaped capsule main body (hereinafter, simply referred to as a main body) 102; a transparent and hemispherical distal end cover 103 made of a soft member, for covering the front edge of the main body 102; and a circular-shaped rear cover 104 for covering the rear end of the main body 102. Thus, the capsule endoscope 101 forms a sealed capsule container with the structure for watertightness, and further includes image pick-up means, etc. which will be described later.

In the capsule container, a CMOS module is formed by attaching a CMOS sensor 105 as the image pick-up means to a sensor substrate 106 in the center thereof, opposed to the distal end cover 103.

A fixing frame 108 having a fixing-side lens 107a of an objective lens system 107 (as a lens as the nearest one from the CMOS sensor 5) is fixed to the side of an image area (image pick-up area) in front of the CMOS sensor 105. A movable frame 110 having a movable-side lens 107b of the objective lens system 107 is fit into a cylindrical portion 108a of the fixing frame 108 for the purpose of the adjustment of the focusing and of the fixing.

A subject image of the luminal portion in the coelom is formed to the image area of the CMOS sensor 105 through the objective lens system 107.

A white LED 111 as illuminating means is mounted on an LED substrate 112 having a hole portion arranged in the center thereof. The hole portion of the LED substrate 112 is fit into and is fixed to the cylindrical portion of the movable frame 110. For example, four white LEDs 111 are arranged to the circumference of an image pick-up range of the objective lens system 107. The four LEDs 111 illuminate the image pick-up range of the objective lens system 107 with substantially uniformity.

A cave portion is formed on the rear surface of the sensor substrate 106. Electric parts such as an IC chip 113 is flip-mounted on the cave portion. The rear surface of the sensor substrate 106 is connected to an image pick-up processing and control substrate 115 via a connecting terminal by using soldering balls 114. The image pick-up processing and control substrate 115 drives the CMOS sensor 105 and performs signal processing and controlling the image picked-up output signal.

A cave portion is formed on the front surface of the image pick-up processing and control substrate 115. A first bear chip 116 as an electric part, e.g., an IC chip is flip-mounted on the cave portion. Further, a second bear chip 117 comprising an IC chip having another function is mounted on the top surface of the bear chip 116 by wire bonding.

The rear surface of the image pick-up processing and control substrate 115 is connected to a communication substrate (radio substrate) 119 via a connecting terminal by a soldering ball 118. Electric parts are mounted on both surfaces of the communication substrate 119, and a Bluetooth-type radio communication module is formed.

As mentioned above, the sensor substrate 106, the image pick-up processing and control substrate 115, and the communication substrate 119 are arranged in the main body 102 in the axial direction thereof. In this case, the sensor substrate 106 and the image pick-up processing and control substrate 115 are electrically connected by the soldering balls 114 at an interval between the soldering balls 114 (in other words, at an interval less than that between the soldering balls 114). Further, the image pick-up processing and control substrate 115 is connected to the communication substrate 119 by the soldering ball 118 at an interval between the soldering balls 118.

The above-mentioned substrates having the different functions are connected at a small interval with high density, and an electric circuit block is formed having an illumination function, an image pick-up function, and a function for transferring the image picked-up signal to the outside. Consequently, the length of the capsule endoscope 101 is short in the axial direction thereof and the capsule endoscope 101 is realized so that a patient easily swallows it.

A part of the side surfaces on the down side of the LED substrate 112, the sensor substrate 106, and the image pick-up processing and control substrate 115 are notched. An antenna 120 connected to the communication substrate 119 is arranged along the notch portions. In this case, the antenna 120 is arranged in parallel with the optical axis O of the objective lens system 107.

The image signal photoelectrically converted by the CMOS sensor 105 is transmitted to an extracorporeal unit (not shown) arranged to the outside via the communication substrate 119, an instruction signal from the extracorporeal unit is received, and the period for illumination or the image pick-up operation is changed.

A battery accommodating unit 121 is formed on the back surface of the communication substrate 119 and the battery accommodating unit 121 accommodates, e.g., three batteries 122.

A flexible substrate 123 as a flexible substrate is arranged along the inner surface of the main body 102 opposed to the antenna 120. The distal end of the flexible substrate 123 is connected to the LED substrate 112, is bent at an angle of approximately 90° by an opening portion 124 arranged on the rear surface side of the communication substrate 119, is inserted in a battery accommodating chamber 121, and comes into contact with the positive of the battery 122 in the halfway thereof (a conductive pattern is exposed in a portion contact with the positive of the battery 122).

The flexible substrate 123 previously has a bending habit so that it is bent at the rear portion of the communication substrate 119 (at the rear end of the communication module 119) and therefore the flexible substrate 123 is easily assembled.

The flexible substrate 123 is bent as mentioned above, is made conductive to the positive of the battery 122 in the halfway thereof, is bent at the angle of 90° along the side surface of the battery accommodating chamber 121 on the antenna 120 side, and is extended backward.

The rear end of the flexible substrate 123 changes from the non-connecting state to the connecting state, or from the connecting state to the non-connecting state, with regard to the front end of a plate spring 125 held onto the inner surface of the cave portion of the rear cover 104 by rotating the rear cover 104. Thus, a power switch 126 is formed to turn off to on, or on to off the power of the battery 122.

The plate spring 125 is L-shaped, approximately U-shaped. The center portion of the plate spring 125 is held to the rear cover 104. Both ends of the plate spring 125 are elastically modified and one end comes into contact with the negative of the battery 122 accommodated in the battery accommodating chamber 121.

The rear cover 104 is moved to the main body 102 side, is rotated at a predetermined angle, is moved in the direction apart from the main body 102, is rotated at a predetermined angle, and is pressed toward the main body 102 side. Thus, referring to FIG. 1A, the front end portion of the plate spring 125 comes into contact with an exposing pattern portion at the rear end of the flexible substrate 123 and, thus, the power of the batteries 122 is supplied to the communication substrate 119, the image pick-up processing and control substrate 115, the sensor substrate 106, and the LED substrate 112 via the power pattern of the flexible substrate 123.

An O-shaped ring 127 for watertightness is inserted between the outer-circumferential surface of the main body 102 and the inner-circumferential surface of the rear cover 104.

A bending portion (play portion) 128 is formed near the distal end of the flexible substrate 123 and it is connected to the LED substrate 112, thereby adjusting the focusing.

FIG. 6B shows a front view of the LED substrate 112 which is viewed in the direction along the optical axis O of the objective lens system 107. As shown in FIG. 6B, a notch portion 131 is arranged to the down bottom of the substantially circular-shaped LED substrate 112 and the distal end of the antenna 120 is arranged in the notch portion 131.

Referring to FIG. 6C showing an A-A cross section in FIG. 6A, the down end side of a polygonal (dodecagonal), namely, approximately circular sensor substrate 106 is notched and the antenna 120 is arranged to the notch portion. Referring to FIG. 6D showing a B-B cross section in FIG. 6A, a notch portion 132 is arranged to the image pick-up processing and control substrate 115 and the antenna 120 is arranged in the notch portion 132.

In this case, referring to FIGS. 6B, 6C, and 6D, the accommodating size of the notch portions 131 and 132 is slightly larger than the width of the antenna 120, and a space arranged along the notch portions 131 and 132 is formed without fixing with a fixing adhesive. Therefore, the antenna 120 is arranged in the sealed capsule with a function for radio communication, that is, with high-frequency oscillation.

Referring to FIG. 6D, a plurality of, e.g., five soldering balls 114 for electrical connection to the sensor substrate 106 are arranged to the image pick-up processing and control substrate 115 along three sides of the left side, the right side, and the upper side opposed to the bottom of the arrangement of the antenna 120 in front of the image pick-up processing and control substrate 115.

As mentioned above, the soldering balls 114 are uniformly arranged to the two to three sides. Consequently, a plurality of electric substrates (here, the image pick-up processing and control substrate 115 and the sensor substrate 106) are electrically connected and are mechanically connected and fixed with ease. Further, the inclination of the substrates is prevented, the deviation of axes is prevented, and the size in the axial direction is reduced (shortened).

As will be understood with reference to FIGS. 6B, 6C, and 6D, the shapes of the LED substrate 112, the sensor substrate 106, and the image pick-up processing and control substrate 115 are substantially circular or polygonal. The maximum outer-diameters of the LED substrate 112, the sensor substrate 106, and the image pick-up processing and control substrate 115 are the same. According to the second embodiment, the maximum outer-diameter thereof are the same. However, the shapes of the LED substrate 112, the sensor substrate 106, and the image pick-up processing and control substrate 115 may be different and, thus, the assembling processing is performed without fail and the confirmation after the assembling is easy.

Referring to FIG. 6A, the distal end side of the antenna 120 is accommodated in the notch portion 131 of the LED substrate 112. However, referring to FIG. 7, the distal end of the antenna 120 may be arranged near the rear surface of the LED substrate 112. In this case, no notch portion 131 may be formed to the LED substrate 112.

Referring to FIGS. 6C and 6D, the top sides of the sensor substrate 106 and the image pick-up processing and control substrate 115 are notched and end surfaces along the notches have connecting terminals 133 connected to a pattern of the flexible substrate 123.

At the above-mentioned interval, the plurality of substrates 112, 106, 115, and 119 arranged in the axial direction of the main body 102 are electrically connected, with ease, to the flexible substrate 123 extended to the axial direction of the main body 102.

By using the flexible substrate 123 as mentioned above, the bending portion 128 (for varying the interval and absorbing the variation if the interval is not constant) is formed and, thus, the interval on the LED substrate 112 side can be changed to the sensor substrate 106 side for the purpose of the focusing adjustment. The flexible substrate 123 may be connected by another member.

According to the second embodiment, the conductive pattern of the flexible substrate 123 is used for a power line connected to a power terminal Vcc and the ground (GND). The soldering balls 114 and 118 are used for a signal transfer line.

In this case, as compared with the soldering balls 114 and 118, the flexible substrate 123 forms a thicker terminal. Advantageously, the thicker terminal of the flexible substrate 123 is used for the power line and the circuits are stable. Further, according to the second embodiment, referring to FIG. 8, the two ore more power lines formed to the flexible substrate 123 are formed separately depending on the connected target functions. Even if the voltage drops due to the one target function, the influence on another function is suppressed and the operation of the circuits is stable.

Figure 8:
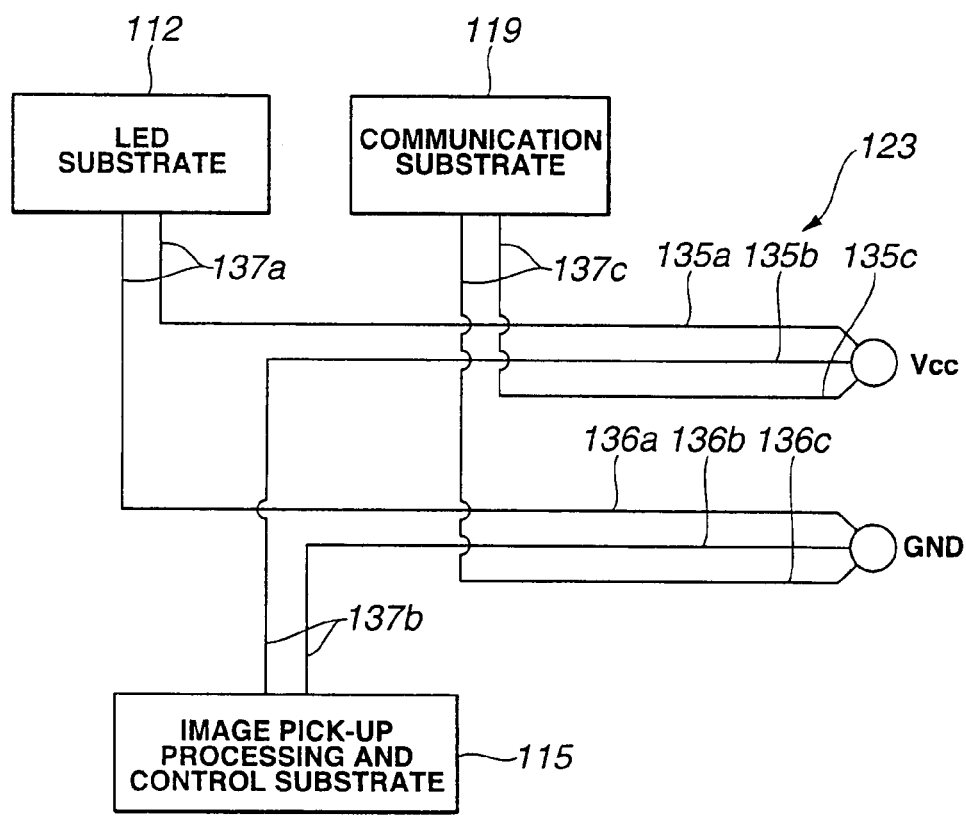

FIG. 8 shows an example of the above case.

Both ends of the flexible substrate 123 are connected to the power terminal Vcc of the battery 122 and the ground GND, respectively. From both the ends, three power line patterns 135a, 135b, and 135c and three power line patterns 136a, 136b, and 136c are separately formed, respectively. The patterns 135a and 136a are connected to the LED substrate 112 as a power line 137a for an illuminating function at the other ends of the flexible substrate 123. The patterns 135b and 136b are connected to the image pick-up processing and control substrate 115 as a power line 137b for an image pick-up processing and control function at the other ends of the flexible substrate 123. The patterns 135c and 136c are connected to the communication substrate 119 as a line 137c for a communication function at the other ends of the flexible substrate 123.

In addition to the case shown in FIG. 8, the power line 137b connected to the image pick-up processing and control substrate 115 is divided into a portion for the image pick-up processing function and a portion for the control function. The portion for the image pick-up processing function and the portion for the control function may be connected to individual power lines.

In addition, the line 137a for the illuminating function comprises the two patterns of the pattern 135a and 136a. However, it may comprise a large number of patterns.

Referring to FIG. 6B, of the four LED substrates 111, the two LED substrates 111 are serially connected on the right and left, respectively. In the case of lighting on the LED substrates 111, the four LED substrates 111 are not simultaneously lit on but the LED substrates 111 are intermittently lit on so that the two LED substrates 111 on the left (designated by reference numeral 111a in FIG. 6E) are lit on and thereafter, synchronously with the light-off thereof, the two LED substrates on the right (designated by reference numeral 111b in FIG. 6E) are lit on.

FIG. 6E shows an explanatory diagram of the intermittent driving of the light-on operation. The LEDs 111a are lit on for a time period Ta and, after that, they are lit off. Then, at the timing for the light-off operation, the LEDs 111b are lit on for the time period Ta and, after that, they are lit off.

A time period Tb as the double of the time period Ta becomes an image pick-up term (exposure term) of the CMOS sensor 105. After passing the time period Tb, the time enters a reading time period Tc for reading the photoelectrically converted signal. After the passage of one second, the LEDs 111a are lit on and then are lit off. At the light-off timing of the LEDs 111a, the LEDs 111b are lit on.

Through the driving of the light operation, as compared with the case for driving the four LEDs, the momentary drop of voltage and the current consumption are suppressed, the influence on the function of another circuit operation is suppressed, and the operation is stable. The large load to the battery 122 is reduced and the shortage of life of the battery 122 is prevented.

Referring to FIGS. 6A and 6D, the first bear chip 116 is flip-mounted on the cave portion of the image pick-up processing and control substrate 115. Further, the second bear chip 117 is mounted on the top surface of the first bear chip 116 by wire bonding. Namely, the two bear chips 116 and 117 are laminated and are mounted.

Figure 9A:
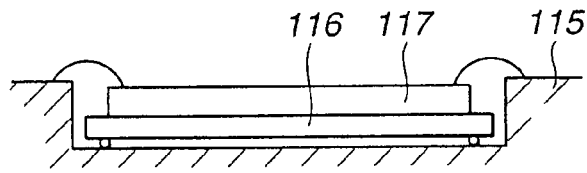
FIG. 9A is an explanatory diagram showing a state for mounting two bear chips.
Figure 9B:
FIG. 9B is a diagram showing a modification of FIG. 9A.

FIG. 9A shows the structure of the cross section in the above case. The foregoing lamination and the mounting with high density realize the small size. In particular, the capsule endoscope 101 has the substantially circular substrate. Consequently, the cave portion is formed in the center of the substrate, the bear chips are laminated and are mounted thereon, and the small size is realized. Referring to FIG. 4, reference symbol FC denotes the flip mounting and reference symbol WB denotes the wire-bonding mounting.

Referring to FIG. 9A, the second bear chip 117 on the top is mounted by wire bonding. On the other hand, referring to FIG. 9B, the first bear chip 116 is flip-mounted. However, the second bear chip 117 may be flip-mounted by making the second bear chip 117 on the top side apart from the upper surface of the first bear chip 116 and by forming, between the apart interval, an air layer 139 having functions for insulation and heat release.

In place of the air layer 139, the high integration (small size) may be realized by inserting an insulting member such as a heat sink having a high function for the heat release and by improving the heat release function.

Reference numeral L1 denotes the entire length of an accommodating portion of the electric circuit unit for the image pick-up operation comprising the distal end cover 103 and the main body 102. Reference numeral L2 denotes the entire length of the electric circuit unit. The dimensions L1 and L2 are determined by satisfying a relation of (L1>L2 or L1=L2) (when compressing force is applied to the inner surface from the outer surface of the distal end portion of the distal end cover 103, it is possible to prevent the damage of the image pick-up means with low strength and the fixing portion of the objective optical system by preventing the direct application of the compressing force to the electric circuit unit).

As will be described hereinbelow with reference to FIG. 10A, the center position of an image area of a CMOS sensor 124 is positioned and is fixed to the center position of a fixing frame 128. Then, a movable frame 130 is adjusted for focusing and is fixed to the fixing frame 128. Further, an image pick-up unit for fixing the LED substrate 112 is positioned and is fixed at the position where a step surface of a distal end cover 103 comes into contact with the end surface of the LED substrate 112. An assembling jig (not shown) positions the image pick-up unit in the circumferential direction. Consequently, the pupil position of an objective lens system 126 is fixed substantially at the center position of the radius of the distal end cover 103.

Further, a main body 121 is positioned and is fixed to the distal end cover 103 having the image pick-up unit via a jig. As a result of positioning, referring to FIG. 6A, the optical axis O of the objective lens system 126 is set to match the central axis O' of the main body 121.

In a capsule endoscope 101 with the above-mentioned structure, the center of the image area of the CMOS sensor 124 is on the optical axis O of the objective lens system 126. The center of the image area is positioned on the central axis of the main body 121. Thus, the images of the CMOS sensor 124 are displayed on a display portion 108a in the same state by setting the individual capsule endoscopes 101 which are different to the same state.

According to the second embodiment, referring to FIG. 6C, the CMOS sensor 105 is almost square-plate-shaped. An image area 141 as an actual image pick-up surface (for photoelectrically converting the received light) is formed in the center of the CMOS sensor 105.

Figure 10A:
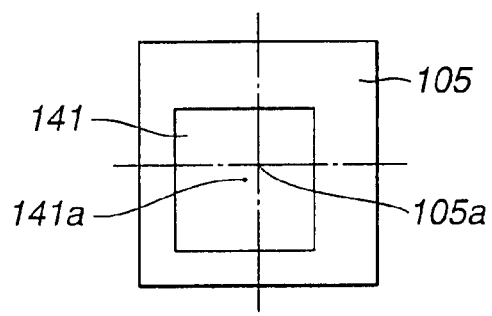
FIGS. 10A to 10C are explanatory diagrams for assembling a sensor substrate around the center of an image area.
Figure 10B:
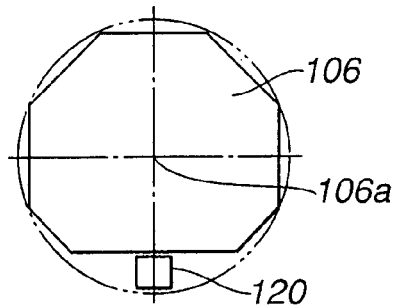
Figure 10C:
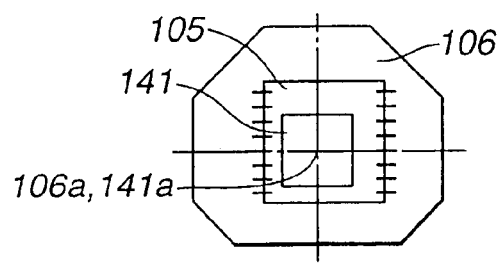

In this case, as schematically shown in FIG. 10A, a center 105a of the CMOS sensor 105 is slightly deviated from a center 141a of the square image area 141. Consequently, according to the second embodiment, referring to FIG. 10B, reference numeral 106a denotes the center of the polygonal, (approximately, circular) sensor substrate 106 (having the CMOS sensor 105). Referring to FIG. 10C, the center 141a of the image area 141 is positioned and is mounted to match the center 106a of the sensor substrate 106.

The sensor substrate 106 is electrically and mechanically connected to the image pick-up processing and control substrate 115 by using the soldering balls 114. Further, the image pick-up processing and control substrate 115 is electrically and mechanically connected to the communication substrate 119 by using the soldering balls 118. The fixing frame 108 is positioned and is fixed to the front surface of the sensor substrate 106. The movable frame 110 is adjusted for focusing and is fixed to the fixing frame 108. The LED substrate 112 is fit into and is fixed to the movable frame 108. Consequently, the (illuminating and) image pick-up unit is formed. The substrates are connected by the flexible substrate 123.

The fixing frame 108 is positioned and is fixed to the front surface of the sensor substrate 106 by using the jig (not shown) so that the center 141a of the image area 141 is positioned on the optical axis O of the fixing-side lens 107a attached to the fixing frame 108.

Figure 11A:
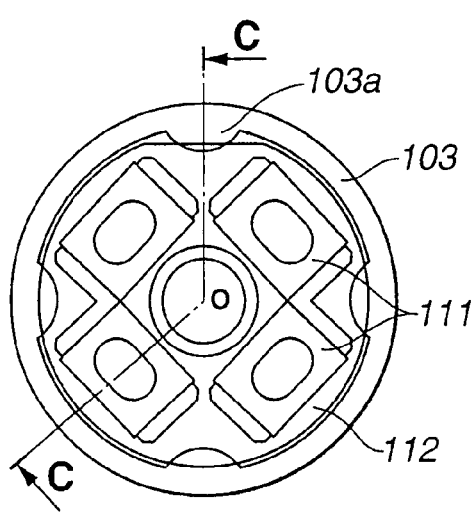
FIG. 11A is a front view showing an overlapped portion between a distal end cover and an LED substrate.

According to the second embodiment, referring to FIG. 11A, a rib 103a is formed with a thicker part in the circumferential direction at the step portion just before the fitting portion at the rear end fit into the main body 102 in the distal end cover 103.

Figure 11B:
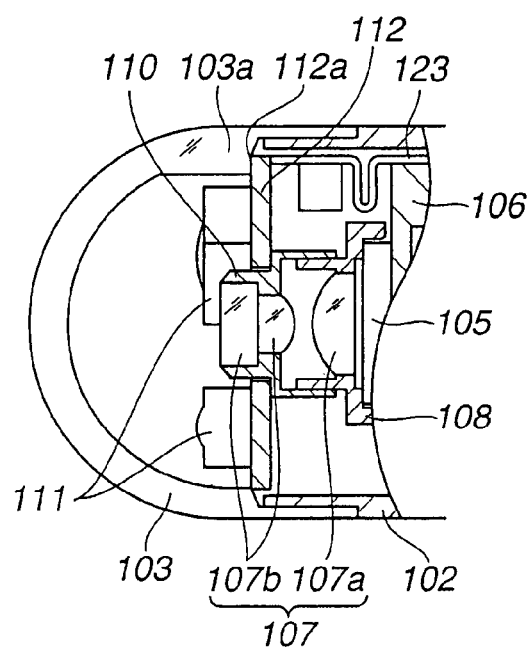
FIG. 11B is a C-O-C cross-sectional view shown in FIG. 11A.

FIG. 11A shows an overlapped portion between the distal end cover 103 and the LED substrate 112 in the front direction. FIG. 11B shows a C-O-C cross section shown in FIG. 11A.

Referring to FIGS. 11A and 11B, the rib 103a is abutted against (an end surface 112a) of the LED substrate 112. Thus, the distal end cover 103 and the image pick-up unit on the LED substrate 112 side are positioned and the distal end cover 103 is fixed.

As a result of the positioning and the fixing, the pupil position of the objective lens system 107 is set to the center position of the hemispherical surface of the distal end cover 103, and it is possible to prevent, from being incident on the objective lens system 107, illumination light from the white LED 111 for illumination arranged around the center position thereof (namely, at the arrangement position largely deviated from the center position of the hemispherical surface of the distal end cover 103). Thus, the generation of flares is prevented.

Next, a description is given of the main assembling processing routine in the assembling method of the capsule endoscope 101 shown in FIG. 6A with reference to FIGS. 12A to 12C.

(1) Referring to FIG. 12A, the distal end cover 103 is inserted into a hole of a jig 151.

(2) After matching indexes of the rib 103a and the jig 151 by rotating the distal end cover 103 (positioning in the circumferential direction), the distal end cover 103 is set as shown in FIG. 11A or 11B. A screw 151a shown in FIG. 12A fixes the distal end cover 103 to the jig 151.

(3) A ring jig 152a is inserted in the inner circumference of the distal end cover 103.

(4) The adhesive is adhered at (e.g., two) points on the LED substrate 112 at the distal end portion of an image pick-up unit 154 shown in FIG. 12A.

(5) After matching indexes of the flexible substrate 123 and the jig 151 by rotating the image pick-up unit 153, the image pick-up unit 153 is inserted into a jig 152a so that the LED substrate 112 is abutted against the distal end cover 103.

(6) Further, a jig 152b is placed the back side of the jig 152a. It is checked that the two jigs 152a and 152b do not extremely intervene in the image pick-up unit 153.

(7) The adhesive is made dry while the jigs 151, 152a, and 152b are attached, and the LED substrate 112 is positioned and is fixed so that it is abutted against the rib 103a of the distal end cover 103.

(8) The jigs 152a and 152b are detached and a jig 154 is placed on the jig 151 as shown in FIG. 12B.

(9) The adhesive is applied to the outer circumference of the distal end portion in the main body 102 and the outer circumference of the communication module in the image pick-up unit 153.

(10) The flexible substrate 123 projected from the rear end of the image pick-up unit 153 is inserted in the main body 102 up to the halfway thereof.

(11) The main body 102 is inserted in the jig 154 (for positioning) and is pressed to be abutted against the distal end cover 103. Consequently, the central axis of the main body 102 is positioned to match the optical axis O of the objective lens system 107.

(12) The main body 102 is rotated so that the flexible substrate 123 is fit into a groove portion 124 of the battery accommodating chamber 121.

(13) The jig 154 is detached and the adhesive protruded to the outer circumference and the bottom surface of the battery accommodating chamber 121 in the main body 102 is wiped off.

(14) The flexible substrate 123 is inserted in the groove of the battery accommodating chamber 121 and is temporarily fixed by using a silver tape.

(15) The jig 151 is fixed and, simultaneously, the adhesive is made dry and is fixed.

(16) The jig 151 is detached, and the adhesive is applied to the rear surface of the flexible substrate 123 and is adhered to the inner surface of the battery accommodating chamber 121.

(17) Referring to FIG. 12C, the jig 155 and the jig 156 are sequentially inserted in the inner circumference of the battery accommodating chamber 121 and the adhesive is made dry.

(18) The jigs 155 and 156 are pulled out, and the flexible substrate 123 is cut off corresponding to the end surface of the battery accommodating chamber 121 of the main body 102.

(19) The three batteries 122 are inserted while the positive (on the plane side) is in the depth direction.

(20) The plate spring 125 is adhered to the bottom surface of the inner-circumferential portion of the rear cover 104, and is made dry.

(21) The O-shaped ring 127 is inserted to the outer circumference of the battery accommodating chamber 121 in the main body 102.

(22) The rear cover 104 is rotated and is inserted in the main body 102. When the rear cover 104 falls in the main body 102, it is rotated in the clockwise direction, thereby turning of the power.

As will be understood from the assembling method, according to the second embodiment, the image pick-up unit 153 is first positioned and fixed to the distal end cover 103. After that, the main body 102 as an exterior casing is positioned and fixed via the jig 154 (further, the rear cover 104 is covered to the rear end of the main body 102), thereby forming the sealed capsule.

According to the second embodiment, referring to FIG. 6A again, reference numeral L1 denotes the entire length of the accommodating portion of the electric circuit unit for the image pick-up operation comprising the distal end cover 103 and the main body 102 as the exterior main body. Reference numeral L2 denotes the entire length of the electric circuit unit accommodated in the accommodating portion. The dimensions L1 and L2 are determined by satisfying the relation of (L1>L2 or L1=L2) (when the compressing force is applied to the inner surface from the outer surface of the distal end portion of the distal end cover 103, it is possible to prevent the damage of the image pick-up means with low strength and the fixing portion of the objective optical system 7 by preventing the direct application of the compressing force to the electric circuit unit).

Figure 13A:
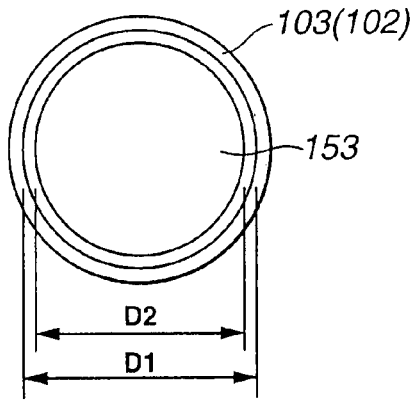
FIGS. 13A and 13B are explanatory diagrams for inner diameters, of the distal end cover and a main body, which are larger than an elastically modified diameter.
Figure 13B:
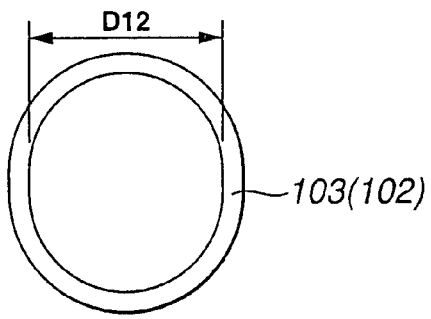

Referring to FIG. 13A, inner diameter D1 and D2 of the distal end cover 103 and the main body 102 are modified to have an elastically modified inner-diameter D12 as shown in FIG. 13B, the dimensions D1 and D2 are determined to satisfy a relation of (D1>D2>D12) where reference number D2 denotes an outer diameter of the electric circuit unit fixedly arranged thereto (even upon applying the compressed force to the capsule from the side, the damage of the distal end cover 103 and the main body 102 is prevented and the watertightness is also realized).

The adhesive made of soft member (such as an elastic silicone system adhesive) fixes the distal end cover 103 and the main body 102 for watertightness upon elastic modification (the watertightness is realized upon adhering the soft members).

Figure 14:
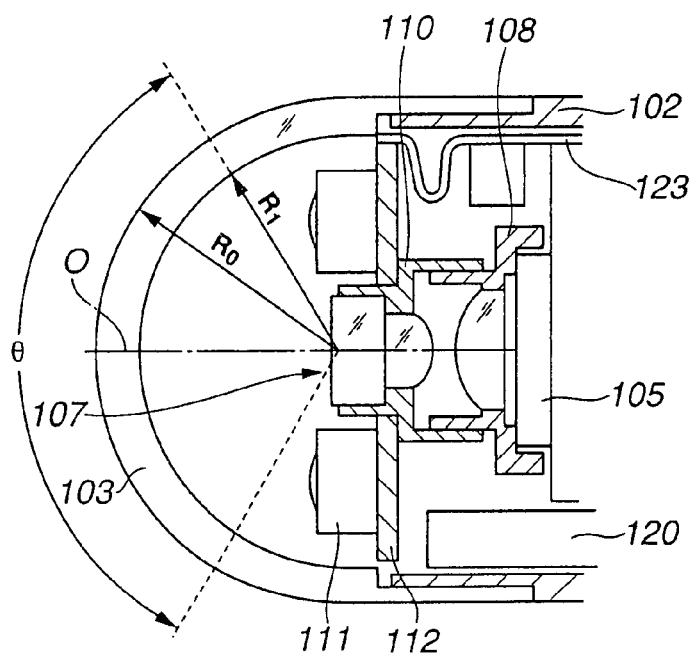

Referring to FIG. 14, according to the second embodiment, reference symbol Ri denotes a curvature radius of the inner surface of the distal end cover 103 and reference numeral Ro denotes a curvature radius of the outer surface thereof within a range of the field-of-view angle θ of the objective lens system 107. The center position of the distal end cover 103 is set substantially at the pupil position of the objective lens system 107, and the thickness of the distal end cover 103 is changed in a portion out of the range (specifically, the thickness is gradually changed to be thinner toward the outer circumference).

The white LED 111 as the illuminating means is arranged at the circumferential position (largely apart from the center position of the distal end cover 103). Thus, it is prevented as much as possible that unnecessary light of the illuminating means enters the field of view so as to obtain a preferable image. Further, the concentration of stress is prevented to suppress the influence on the field of view.

In the above-stated assembling method and structure of the capsule endoscope 101, the sensor substrate 106, the image pick-up processing and control substrate 115, and the communication substrate 119 are mounted on the capsule with high density, and the capsule endoscope 101 is small in size and is easily swallowed.

The pupil position of the objective optical system is set at the center positions of the inner diameter and the outer diameter of the distal end cover 103 to obtain the image with the suppressed influence of flares. Further, the center of the image area of the image pick-up means is set on the optical axis of the objective optical system and the optical axis matches the central axis of the cylindrical member of the main body 102. Thus, it is possible to provide the capsule endoscope 101 with preferable characteristics that the variation in quality of the picked-up image is suppressed.

Third Embodiment

Figure 15:
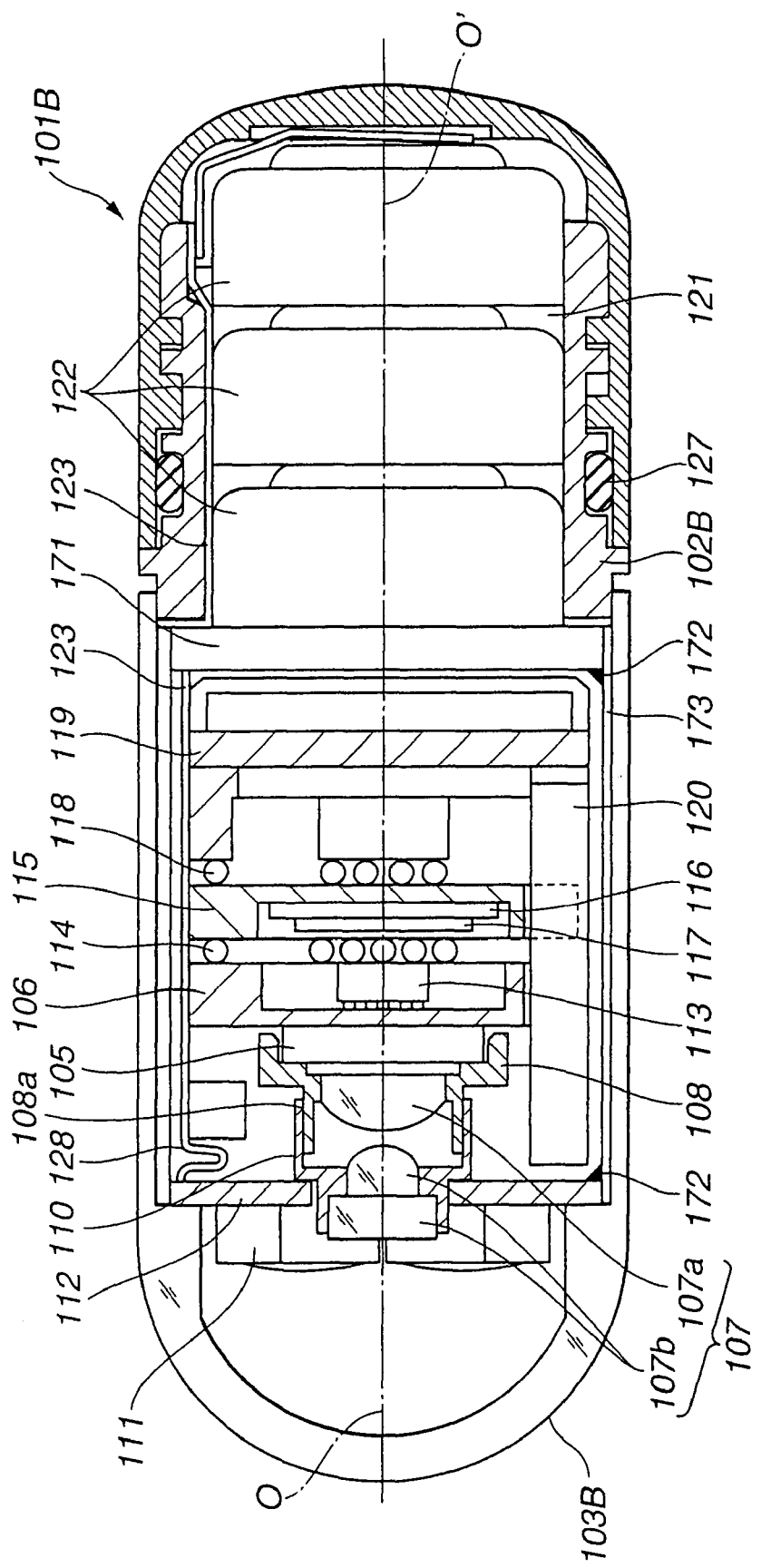
FIG. 15 is a longitudinal cross-sectional view showing a capsule endoscope according to a third embodiment of the present invention.

FIG. 15 shows a capsule endoscope 101B according to a third embodiment of the present invention.

Figure 7:
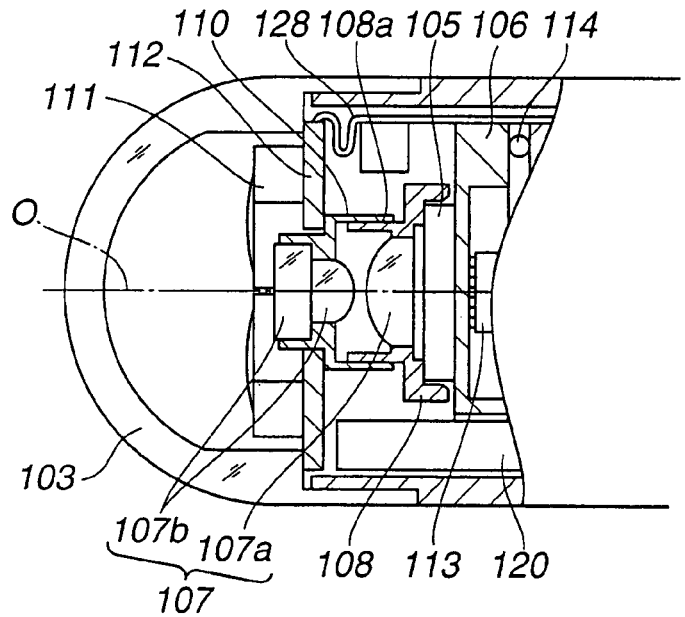

Referring to FIG. 15, in the capsule endoscope 101B according to the third embodiment, the distal end cover 103 in the capsule endoscope shown in FIG. 7 is prolonged, thereby forming a distal end cover 103B. The rear end of the distal end cover 103B is fit into and is connected to a short main body 102B having the battery accommodating chamber 121. Further, with the structure in which a rear substrate 171 is arranged at the rear end of the communication module, the structure for watertightness in the distal end cover 103B may be formed by adhering, with the distal end cover 103B, an adhesive 172 to the partial circumference of the LED substrate 112 and the rear substrate 171.

According to the third embodiment, the flexible substrate 123 in the distal end cover 103B is connected to the flexible substrate 123 on the main body 102B side via the rear substrate 171.

Referring to FIG. 15, a cylindrical member 173 is arranged to the inside of the distal end cover 103B. However, the distal end cover 103B may be formed for watertightness by using the adhesive 172 without the cylindrical member 173, on the inner-circumferential surface of the distal end cover 103B and around the partial circumference of the LED substrate 112 and the rear substrate 171. According to the third embodiment, the same advantages as those according to the second embodiment are obtained.

As stated above, according to the second and third embodiments, in the capsule endoscope comprising at least the illuminating means, the image pick-up means for picking up the portion illuminated by the illuminating means, and the objective optical system in front of the image pick-up means in the sealed capsule, the electric circuit block is arranged, in which a plurality of substrates having different functions are connected by the connecting terminal at the interval less than that between the connecting terminals. Therefore, it is possible to realize the capsule medical apparatus such as the capsule endoscope, which has the arrangement of necessary functions with high density and which is easily swallowed.

Fourth Embodiment

Next, a fourth embodiment of the present invention will be described with reference to FIGS. 16 to 19. According to the fourth embodiment, it is possible to provide a capsule medical apparatus in which a plurality of electric substrates are precisely connected in parallel with each other and the assembling performance is preferable with small size.

Figure 16:
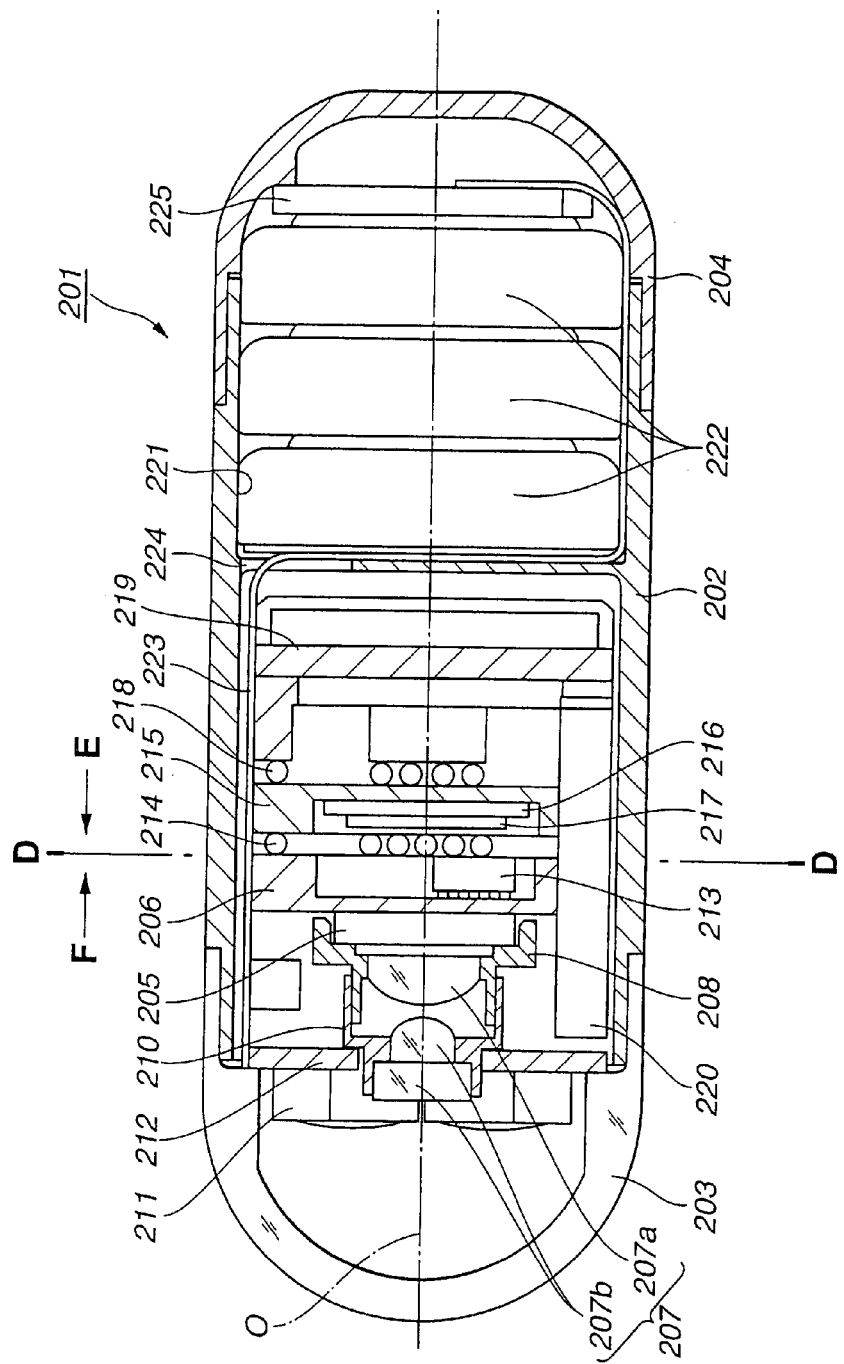

Referring to FIG. 16, in a capsule endoscope 201 according to the fourth embodiment, the front end of a cylindrical capsule main body (hereinafter, abbreviated to a main body) 202 is covered with a transparent and hemispherical distal end cover 203 which is made of a soft member. The rear end of the main body 202 is covered with a rear cover 204 which is circular-shaped, thereby forming a sealed capsule container with the structure for watertightness. Further, the capsule endoscope 201 incorporates image pick-up means and the like.

In the center of the capsule container, a CMOS sensor 205 as the image pick-up means is attached to a sensor substrate 206 opposed to the distal end cover 203, thereby forming a CMOS module.

A fixing-side lens system 207a (as a lens arranged to the most adjacent portion of the CMOS sensor 205) of the objective lens system 207 is arranged to a fixing frame 208. The fixing frame 208 is fixed to the image area (picked-up area) side on the front surface of the CMOS sensor 205. A movable-side lens 207b of the objective lens system 207 is attached to a movable frame 210. The movable frame 210 is fit into a cylindrical portion of the fixing frame 208, is adjusted for focusing, and is fixed.

The objective lens system 207 forms a subject image of the luminal portion in the coelom onto the image area of the CMOS sensor 205 in an in-focus state.

A white LED substrate 211 as illuminating means is mounted on an LED substrate 212 having a hole portion arranged in the center of the cylindrical portion of the movable frame 210. The hole portion is fit into and is fixed to the cylindrical portion of the movable frame 210. For example, four white LEDs 211 are arranged to the circumference of an image pick-up range of the objective lens system 207. The four LEDs 211 illuminate the image pick-up range of the objective lens system 207 with substantially uniformity.

A cave portion is formed on the rear surface of the sensor substrate 206. Electric parts such as an IC chip 213 is flip-mounted on the cave portion. Further, a driving circuit for driving the CMOS sensor 205 is formed on the rear surface of the sensor substrate 206. The rear surface of the sensor substrate 206 is connected to an image pick-up processing and control substrate 215 via connecting terminals by using soldering balls 214. The image pick-up processing and control substrate 215 performs signal processing and control processing of the output signal which is picked-up by the CMOS sensor 205.

A cave portion is formed on the front surface of the image pick-up processing and control substrate 215. A first bear chip 216 as an electric part, e.g., an IC chip is flip-mounted on the cave portion. Further, a second bear chip 217 comprising an IC chip having a different function is mounted on the top surface of the first bear chip 216 by wire bonding.

The rear surface of the image pick-up processing and control substrate 215 is connected to a communication substrate (radio substrate) 219 via connecting terminals by soldering balls 218. Electric parts are mounted on both surfaces of the communication substrate 219, and a Bluetooth-type radio communication module is formed.

The sensor substrate 206, the image pick-up processing and control substrate 215, and the communication substrate 219, which have different functions, are arranged in the main body 202 in the axial direction thereof. In this case, the sensor substrate 206 and the image pick-up processing and control substrate 215 are electrically connected by the soldering balls 214 at an interval therebetween (in other words, at an interval less than that between the soldering balls 214). Further, the image pick-up processing and control substrate 215 is connected to the communication substrate 219 in parallel with each other by the soldering balls 218 at an interval therebetween. Thus an electrical circuit block is formed.

The substrates having the different functions are connected at a small interval with high density, and an electric circuit block is formed having an illumination function, an image pick-up function, and a function for transferring the image picked-up signal to the outside. Consequently, the length of the capsule endoscope 201 is short in the axial direction thereof and the capsule endoscope 201 is realized so that a patient easily swallows it.

A part of the side surfaces on the down side of the LED substrate 212, the sensor substrate 206, and the image pick-up processing and control substrate 215 are notched. An antenna 220 connected to the communication substrate 219 is arranged along the notch portion. In this case, the antenna 220 is arranged in parallel with the optical axis O of the objective lens system 207.

The image signal photoelectrically converted by the CMOS sensor 205 is transmitted to an extracorporeal unit (not shown) arranged to the outside via the communication substrate 219, an instruction signal from the extracorporeal unit is received, and the periods for illumination and the image pick-up operation are changed.

On the back surface of the communication substrate 219, a battery accommodating unit 221 comprises the main body 202 and the rear cover 204. The battery accommodating unit 221 accommodates three batteries 222.

A flexible substrate 223 is arranged along the inner surface of the main body 202 opposed to the antenna 220. The distal end of the flexible substrate 223 is connected to the LED substrate 212, is bent at an angle of approximately 90° by an opening portion 224 arranged on the rear surface side of the communication substrate 219, is inserted in a battery accommodating chamber 221, and comes into contact with the positive of the battery 222 in the halfway thereof (a conductive pattern is exposed to a portion contact with the positive of the battery 222).

The flexible substrate 223 previously has a bending habit so that it is bent at the rear portion of the communication substrate 219 (at the rear end of the communication module) and, therefore, the flexible substrate 223 is easily assembled.

The flexible substrate 223 is bent as mentioned above, is made conductive to the positive of the battery 222 in the halfway thereof, is bent at the angle of 90° along the side surface of the battery accommodating chamber 221 on the antenna 220 side, and is extended backward.

The rear end of the flexible substrate 223 is connected to a switch substrate 225 arranged between the negative of the battery 222 and the inner surface of a cave portion of the rear cover 204.

The switch substrate 225 has a sensor for detecting ambient light and magnetic force in a non-contact state and a switch circuit for turning on/off by an output as a result of the detection of the sensor. The ambient light and magnetic force switch on/off a switch via the switch circuit. Further, the switch substrate 225 has a power switch for changing from off-operation to on-operation of the power from the battery 222, or changing from the on-operation to the off-operation.

A part of the side surfaces on the down side of the LED substrate 212 and the sensor substrate 206 are notched. The antenna 220 connected to the communication substrate 219 is arranged along the notch portion. In this case, the antenna 220 is arranged in parallel with the optical axis O of the objective lens system 207.

Figure 17A:
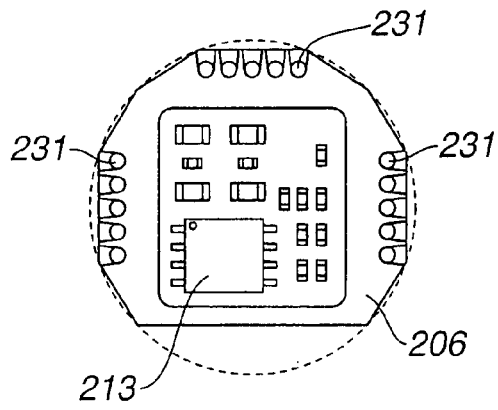
FIGS. 17A and 17B are diagrams showing the structure of two electric substrates at the position on a D-D cross-section shown in FIG. 16 in directions of arrows E and F.
Figure 17B:
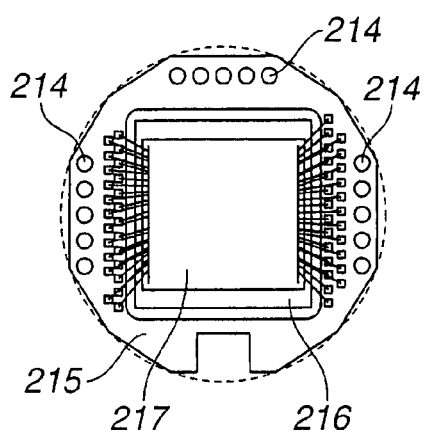

A description is given of the electrically conductive state and the mechanical fixing structure of the substrates with reference to FIGS. 17A and 17B. FIG. 17A shows the back surface of the sensor substrate 106 in an arrow D direction on the C-C cross section shown in FIG. 16. FIG. 17B shows the front surface of the image pick-up processing and control substrate 215 in an arrow E on the C-C cross section shown in FIG. 16.

Referring to FIGS. 17A and 17B, the exterior shapes of the sensor substrate 206 and the image pick-up processing and control substrate 215 are polygonally formed with the diameters slightly smaller than the inner diameter of the cylindrical main body 202. In this case, the antenna 220 is arranged on the bottom and, therefore, the exterior shapes are notched.

The sensor substrate 206 is a cavity substrate with a step in which a cave portion is formed in the center of the back surface thereof. The image pick-up processing and control substrate 215 is a cavity substrate with the step in which a cave portion is formed in the center of the front surface thereof.

The IC chip 213 forming the driving circuit of the CMOS sensor 205 is mounted on the cave portion of the sensor substrate 206. A plurality of pads 231 are formed around the back surface of the sensor substrate 206, specifically, on the upper side and right and left sides thereof, and the sensor substrate 206 is fused and is connected to the image pick-up processing and control substrate 215 at the pads 231 by the soldering balls 214 to electrically be connected to the image pick-up processing and control substrate 215. By hardening processing after the fusion, the sensor substrate 206 is fixed to the image pick-up processing and control substrate 215 at the soldering balls 214 with mechanically high strength.

In this case, the pads 231 on the sensor substrate 206 side are extended to the exterior portions thereof. Specifically, the pads 231 are extended to the upper side and the right and left sides, and the soldering balls 214 are easily fused by soldering iron. That is, in a space between the substrates is small and, therefore, it is not possible to directly fuse the soldering balls by inserting the distal end of the soldering iron between the substrates.

On the other hand, the pads 231 reaching the sides are arranged and, thus, a jig (not shown) holds the sensor substrate 206 and the image pick-up processing and control substrate 215 so that the exterior shapes thereof are matched. The distal end of the soldering iron is abutted on the side portion of the sensor substrate 206 and thus heat is easily transmitted to the pads 231 made of copper foil or gold foil. Further, the heat is transmitted to the soldering balls 214 contact with the pads 231 and, thus, the soldering balls 214 are easily fused for soldering operation. Therefore, the soldering operation is easily performed for a short time and the operability is improved.

The pads 231 on the upper side facilitates the electric connection to the flexible substrate 223 arranged along the upper side.

As mentioned above, for example, five soldering balls 214 are uniformly arranged to the two or three sides of the sensor substrate 206. Consequently, a plurality of electric substrates (here, the image pick-up processing and control substrate 215 and the sensor substrate 206) are electrically connected, and are mechanically connected and fixed with ease. The inclination of substrates is prevented by the small space and the substrates are held in parallel with each other. Further, the deviation of axes is prevented and, in particular, the size in the axial direction is reduced with high-density mounting.

Referring to FIGS. 16 and 17B, the first bear chip 216 is flip-mounted on the cave portion of the image pick-up processing and control substrate 215. Further, the second bear chip 217 is mounted on the top surface of the first bear chip 216 by wire bonding. Namely, the two first and second bear chips 216 and 217 are laminated and are mounted. With the above-mentioned multi-layer structure, the circuit is mounted with high density and the size of the capsule endoscope 201 is reduced.

The image pick-up processing and control substrate 215 is connected and is fixed to the communication substrate 219 by using the soldering balls 218.

Figure 18:
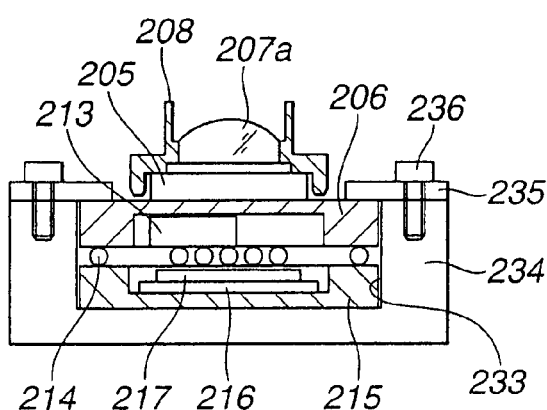

FIG. 18 shows means for assembling the sensor substrate 206 and the image pick-up processing and control substrate 215 according to a modification of the fourth embodiment.

The fixing frame 208 having the fixing-side lens 207*a* is fixed to the CMOS sensor 205 on the front surface thereof. The CMOS sensor 205 is mounted on the sensor substrate 206. The sensor substrate 206 is overlappingly arranged to the image pick-up processing and control substrate 215 by inserting the soldering balls 214 in a cave portion 233 of a first fixing jig 234 for positioning and matching the outer shapes of the sensor substrate 206 and the image pick-up processing and control substrate 215.

Further, a fixing jig 235 for temporary fixing is overlapped and is fixed to the first fixing jig 234 by using a screw 236. Thus, the sensor substrate 206 and the image pick-up processing and control substrate 215 are temporarily fixed in the precisely positioned state. On the plate-shaped fixing jig 235 side, a portion for pressing the sensor substrate 206 may be made of an elastic spring member.

In this case, referring to FIGS. 17A and 17B, the sensor substrate 206 and the image pick-up processing and control substrate 215 have almost the same outer shape. Corresponding to the same outer shape of the sensor substrate 206 and the image pick-up processing and control substrate 215, the inner shape of the cave portion 233 of the first fixing jig 234 is set. Therefore, when the sensor substrate 206 and the image pick-up processing and control substrate 215 are overlappingly accommodated in the cave portion 233, both the sensor substrate 206 and the image pick-up processing and control substrate 215 are set in parallel with each other in accurately positioned state. The positions of the sensor substrate 206 and the image pick-up processing and control substrate 215 are temporarily fixed by the screw 236.

The temporarily-fixed substrate unit (hereinafter, referred to as an image pick-up unit for the sake of convenience) enters a reflow furnace which is moved on a conveyor belt (not shown), and is subjected to soldering processing.

Figure 19:
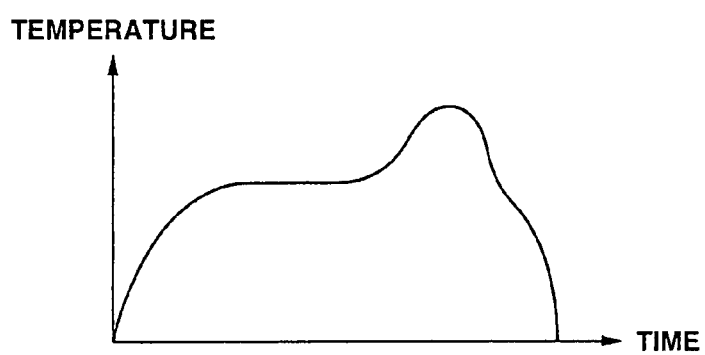

Referring to FIG. 19, the image pick-up unit is subjected to heating processing by using the reflow furnace in accordance with a profile of a predetermined temperature characteristic. A flux of the soldering balls 214 is fused, after that, the image pick-up unit is further heated, and the solder is fused. The above heating processing is sequentially performed. The soldering balls 214 make the image pick-up unit electrically conductive. Upon hardening the fused soldering balls 214, the image pick-up unit is mechanically connected and fixed.

In the case shown in FIG. 18, the CMOS sensor 205, the fixing-side lens 207*a*, and the fixing frame 208 are made of a material having the tolerance for the heating processing for soldering using the reflow furnace.

When the fixing-side lens 207*a* is not made of glass but of a member having no tolerance for the heating processing for soldering of resin or having low tolerance, only the sensor substrate 206 and the image pick-up processing and control substrate 215 in FIG. 18 are soldered by the reflow furnace. Then, the CMOS sensor 205 as the image pick-up means or the fixing frame 208 having the fixing-side lens 207*a* may be mounted on the sensor substrate 206.

In other words, upon assembling the sensor substrate 206 and the image pick-up processing and control substrate 215 by using the member of the image pick-up means having low heat resistance, the substrates may be subjected to the soldering processing with the reflow furnace and, thereafter, the member having low heat resistance of the image pick-up means may be assembled.

FIG. 18 shows the structures of the sensor substrate 206 and the image pick-up processing and control substrate 215 which are subjected to the heating processing for soldering with the reflow furnace by the first and second fixing jigs 234 and 235. However, the soldering processing may be performed with the reflow furnace by laminating the communication substrate 219 in addition to the sensor substrate 206 and the image pick-up processing and control substrate 215, namely, by temporarily fixing the three substrates.

The heating processing for soldering is performed by using the reflow furnace. Then, upon mass-production of the capsule endoscope 201, the products thereof are manufactured with the same quality and low costs.

The soldering processing is not limited to that with the reflow furnace. The image pick-up unit may be accommodated in a heating furnace and may be subjected to the soldering processing through the heating processing with a temperature characteristic as shown in FIG. 19.

According to the fourth embodiment, a plurality of substrates have the small intervals via the connecting members such as the soldering balls and are arranged in parallel to be made electrically conductive. Further, the plurality of substrates are mechanically connected and are fixed, and are thus mounted with high density. Consequently, it is possible to realize the capsule endoscope which is easily swallowed with the small size and performs the medical action using endoscope examination.

As compared with the case in which the substrates are electrically conductive by making them contact or close to each other, the mechanical strength is high and the stable operation is possible because the substrates are electrically connected and are mechanically fixed.

Additionally, when the substrates are not assembled in parallel with each other, namely, are inclined, they are inclined with the lengths thereof which are long in the longitudinal direction. The sizes of the substrates in the radius direction orthogonal to the longitudinal direction are partially long. Therefore, as the variation in length and size becomes larger, the inner diameter of the cylindrical capsule main body 202 should be set to be increased.

Further, for the purpose of low costs, the fixing-side lens 207*a* is made of a member, such as resin, which is easily mass-produced but has low tolerance for heat. Then, the plurality of substrates are subjected to the soldering processing. Thereafter, the objective lens system 207 and the CMOS sensor 205 are assembled to the substrates. In the above-mentioned case, the inclination of the assembled substrates, namely, no parallel state thereof causes the assembling operation with precisely positioned optical axis O to become troublesome.

On the contrary, according to the fourth embodiment, the substrates have the same exterior shape in the state parallel with each other and are subjected to the soldering. Further, since the substrates are not inclined, the optical axis O is accurately positioned and the operation for assembling the objective lens system 207 and the CMOS sensor 205 becomes easy. In addition, the interval between the substrates is reduced and the mounting operation is realized with high density.

Fifth Embodiment

Figure 20:
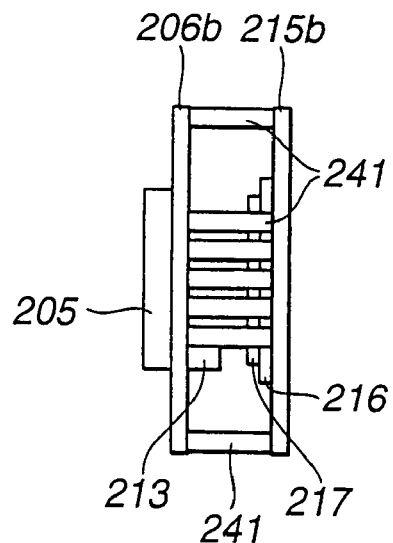

Next, a fifth embodiment of the present invention will be described with reference to FIGS. 20 to 24. FIG. 20 shows an example of assembling a plurality of substrates according to the fifth embodiment.

According to the fourth embodiment, the soldering balls 214 and 218 are used as the connecting members for connecting and fixing the substrates. However, according to the fifth embodiment, pins 241 are used as shown in FIG. 20.

Specifically, both ends of a plain sensor substrate 206*b* and a plain image pick-up processing and control substrate 215*b* are abutted, via the pins 241, against pads substantially vertical thereto (not shown, arranged to opposed portions) of the sensor substrate 206*b* and the image pick-up processing and control substrate 215*b*. The sensor substrate 206*b* and the image pick-up processing and control substrate 215*b* keeps a predetermined interval therebetween in parallel with each other and are connected by the soldering (incidentally, the connection and fixing mean the electric conductive state and the mechanical fixing, as mentioned above).

According to the fifth embodiment, the CMOS sensor 205 is mounted on the front surface of the plain sensor substrate 206*b*. The IC chip 213 is mounted on the rear surface of the sensor substrate 206*b*. The first bear chip 216 is flip-mounted on the front surface of the plain image pick-up processing and control substrate 215*b* and, further, the second bear chip 217 is mounted on the top surface of the first bear chip 216 by wire bonding.

The two sensor substrate 206*b* and image pick-up processing and control substrate 215*b* are connected and fixed by soldering with the pins 241 made of an electrically conductive metal at a predetermined interval, specifically, at an interval having at least the total thickness of the IC chip 213 and the first and second bear chips 216 and 217.

When parts such as the IC chip 213 are mounted on the electrical substrate such as the sensor substrate 206, the height of the soldering ball as the connecting member is shorter than the mounted part, upon soldering the sensor substrate 206 to another substrate on the mounting side. Therefore, the electrical substrate needs to have the above-mentioned step structure (cavity structure).

On the other hand, according to the fifth embodiment, the electrical substrate may have the plain structure by using the pins 241, and the expensive cavity substrate is unnecessary. Advantageously, costs are reduced because the use of the pins 241 results in the unnecessary situation of the expensive cavity substrate as the plain electrical substrate.

Figure 21A:
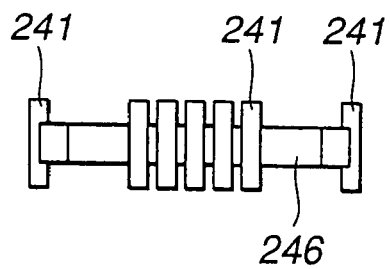
FIGS. 21A and 21B are a side view and a plan view showing a connecting member according to a first modification of the fifth embodiment.
Figure 21B:
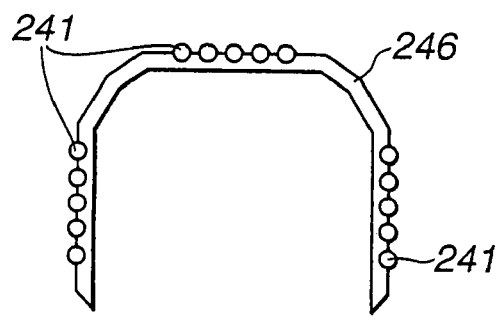

FIGS. 21A and 21B show a side view and a plan view of the connecting member according to a first modification of the fifth embodiment.

According to the first modification, the plurality of pins 241 shown in FIG. 20 are positioned and are fixed on the side surface of a holding frame member 246 which is insulative and is U-shaped. The plurality of pins 241 integrated with the holding frame member 246 connect and fix the sensor substrate 206*b* and the image pick-up processing and control substrate 215*b* as shown in FIG. 20.

According to the first modification, the plurality of pins 241 are integrated with the holding frame member 246 and, thus, the pins 241 are not moved upon soldering. Therefore, the operability is improved.

Figure 22A:
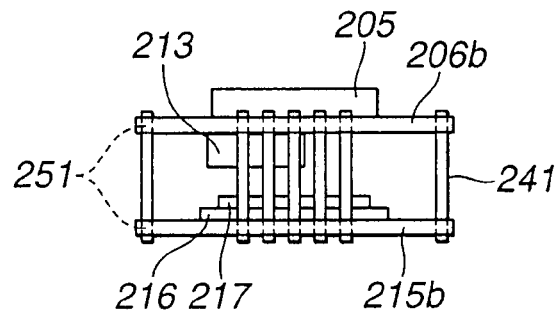
FIGS. 22A to 22C are a side view, a plane view, and a bottom view showing an example of the structure for assembling the substrate according to a second modification.
Figure 22B:
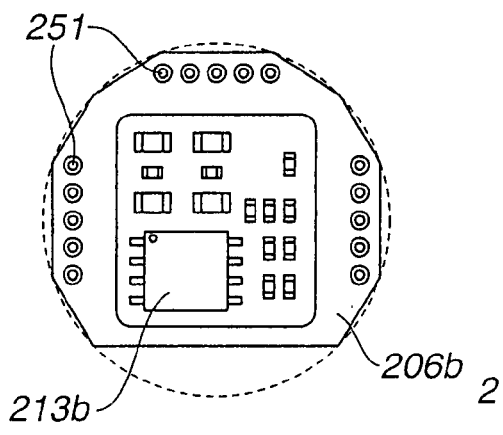
Figure 22C:
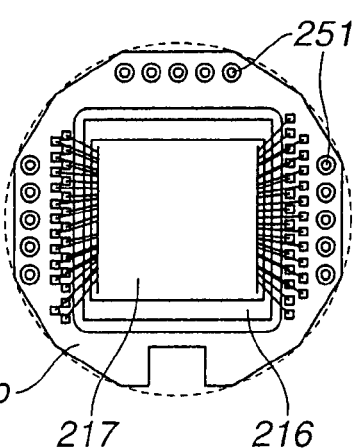

FIGS. 22A to 22C show explanatory diagrams showing the structure of assembling the plurality of substrates according to a second modification. FIG. 22A is a side view thereof, FIG. 22B is a plan view thereof, and FIG. 22C shows a bottom view thereof.

According to the second modification, referring to FIGS. 22B and 22C, the sensor substrate 206*b* and the image pick-up processing and control substrate 215*b* have fitting holes 251 for fitting and piercing the pins 241, respectively. End portions of the pins 241 are pierced in the corresponding fitting holes 251. Then, referring to FIG. 22A, the sensor substrate 206*b* and the image pick-up processing and control substrate 215*b* are connected and are fixed by soldering.

According to the second modification, the pins 241 are fit into the fitting holes 251. Thus, the pins 241 do not need to vertically stand on the surface of the electrical substrate and the operability is improved.

Figure 23:
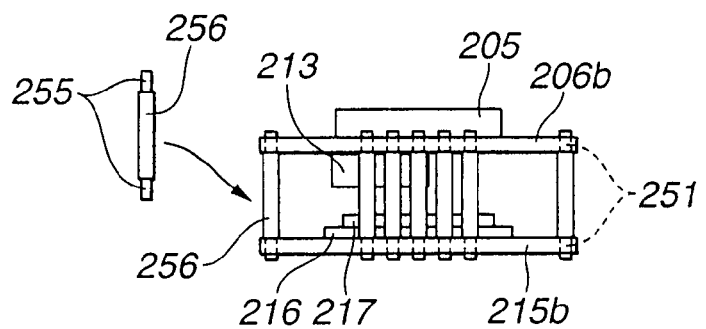

FIG. 23 shows a third modification of the fifth embodiment. Specifically, FIG. 23 corresponds to the modification of the second modification of FIGS. 22A to 22C. According to the third modification, in place of the pins 241 shown in FIGS. 22A to 22C, pins 256 with steps are used. The pins 256 with steps have step portions 255 near both ends thereof.

A portion in the center in the longitudinal direction is made thicker like a step, as compared with both the ends fit into the fitting holes 251 shown in FIGS. 22A to 22C. The sensor substrate 206*b* and the image pick-up processing and control substrate 215*b* are maintained to have a predetermined interval by using the thicker step portions 255, and a portion projected from the fitting hole 251 is connected and is fixed by soldering.

The clearance between the electrical substrates is easily kept to have the predetermined interval by using the step portions 255 with the pins 256 with steps. Further, the substrates are connected and are fixed in parallel with each other by soldering.

Figure 24:
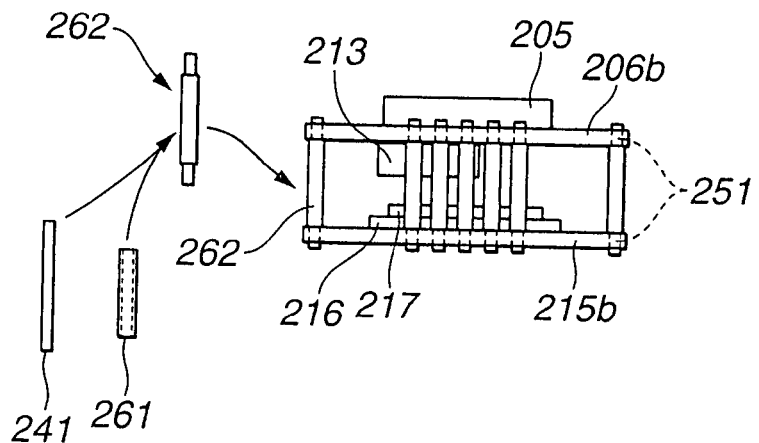

FIG. 24 shows a fourth modification of the fifth embodiment. Specifically, FIG. 24 corresponds to the modification of the second or third modification of FIGS. 22A to 22C or FIG. 23. According to the fourth modification, in addition to the pins 241, tube-shaped spacers 261 are arranged each having a hollow portion for fitting of the pins 241. Consequently, pins 262 with steps are used having the same function as that of the pin 256 with the step shown in FIG. 23, and the sensor substrate 206*b* and the image pick-up processing and control substrate 215*b* are connected and are fixed by soldering.

According to the fourth modification of the fifth embodiment, the pins 241 are fit into the fitting holes 251 of the electrical substrate and the tube-shaped spacers 261 keep the clearance of the electrical substrates. The fourth modification has the same advantages as those of the third modification.

Sixth Embodiment

Figure 25:
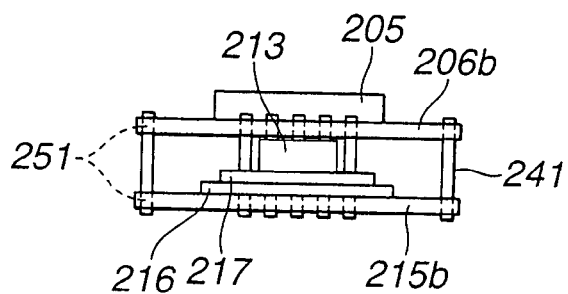

Next, a sixth embodiment of the present invention will be described with reference to FIGS. 25 to 28B. FIG. 25 shows the structure for connecting and fixing substrates according to the sixth embodiment. Basically, the sixth embodiment has the same structure as that shown in FIGS. 22A to 22C.

According to the sixth embodiment, the IC chip 213, the first bear chip 216, and the second bear chip 217 are layered, maintain a predetermined interval there among, and are connected and are fixed by soldering with the pins 241 pierced through the fitting holes 251.

In this case, the mounting position of the IC chip 213 (the circuit pattern on the sensor substrate 206 side) is set to be layered to the first bear chip 216 and the second bear chip 217 with a wide area. The parallel degree up precisely layering the chips is improved and the soldering is performed by using the pins 241.

According to the sixth embodiment, the clearance of the substrates keeps a predetermined interval therebetween by abutting parts mounted on the substrates against each other without the pins having the steps. Simply, the straight pins 241 may be used and the costs are reduced.

Figure 26:
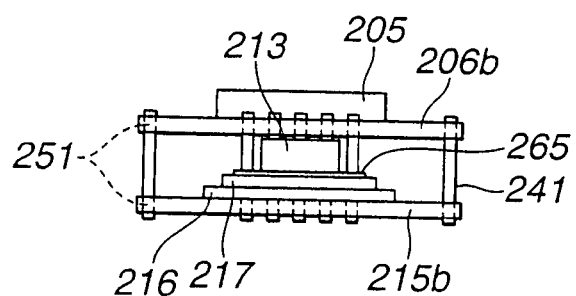

FIG. 26 shows a first modification of the sixth embodiment. According to the first modification, referring to FIG. 25, when a conductive member is exposed onto the contact surface between the IC chip 213 and the second bear chip 217, the insulating sheet 265 such as a mica plate is inserted between the chips. The short-circuit is prevented upon abutting the parts against each other as mentioned above.

Figure 27A:
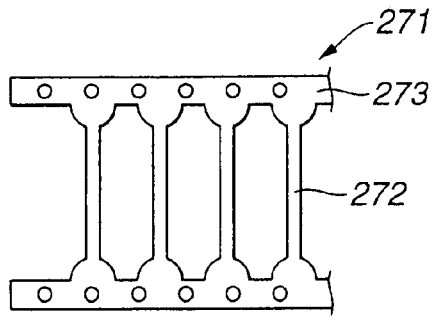
FIG. 27A is a diagram showing a lead frame used as a connecting member according to a second modification.
Figure 27B:
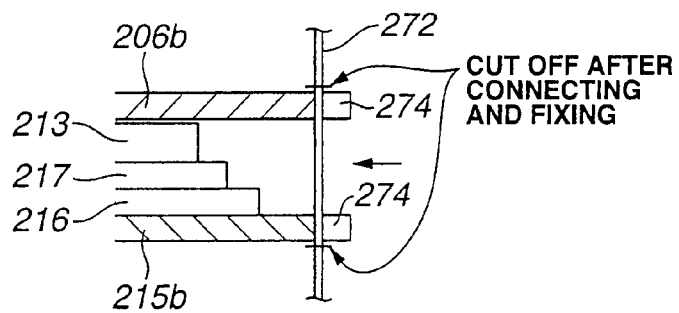
FIG. 27B is a diagram showing one example of the structure for assembling the substrates by processing the lead frame.

FIGS. 27A and 27B show a second modification of the sixth embodiment. FIG. 27A shows a lead frame 271 used as a connecting member. FIG. 27B shows a state for connecting and fixing the sensor substrates 206b and the image pick-up processing and control substrate 215b.

Referring to FIG. 27A, according to the second modification, the lead frame 271 is used for manufacturing dual-in-line IC chips. Both ends of the lead frames 271 are integrally formed to frame portions 273 in the lead frames 271 at a predetermined interval.

According to the second modification, referring to FIG. 27B, the lead portions 272 are plunged, from the side direction, into connecting portions 274 which are obtained by notching end portions of the sensor substrates 206b and the image pick-up processing and control substrate 215b like a slit, and the soldering is performed. In this case, the connecting portions 274 have conductive portions connected to the patterns at the side surface portion or top surface and bottom surface thereof.

In this case, the sensor substrates 206b and the image pick-up processing and control substrate 215b keeps the predetermined interval therebetween by setting the IC chip 213, the first bear chip 216, and the second bear chip 217 to be layered. As mentioned above, the sensor substrates 206b and the image pick-up processing and control substrate 215b are connected and fixed by soldering at, e.g., five portions thereof. Then, the projected lead portion is cut off.

According to the second modification, the lead 272 is integrated. Advantageously, the operability is improved upon soldering at a plurality of portions for a short time.

Figure 28A:
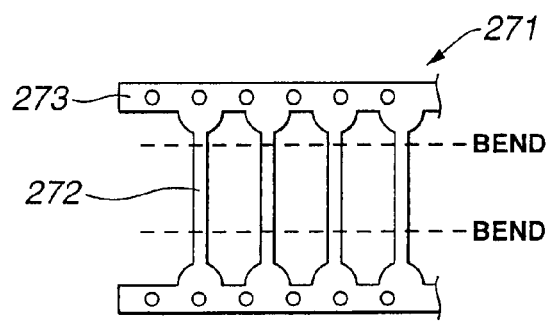
FIG. 28A is a diagram showing a lead frame used as a connecting member according to a third modification.
Figure 28B:
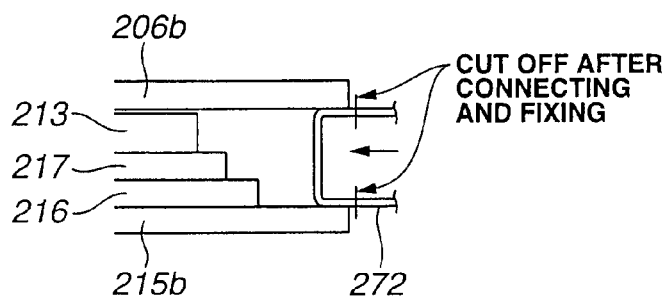

FIGS. 28A and 28B show a third modification of the sixth embodiment. FIG. 28A shows the lead frame 271 used as a connecting member, similarly to the case shown in FIG. 27A. FIG. 28B shows a state for connecting and fixing the sensor substrates 206b and the image pick-up processing and control substrate 215b.

Referring to FIG. 28A, according to the third modification, the lead frame 271 is used and has leads 272 at a predetermined interval therebetween, which are integrally formed to the frame portions 273 at both ends thereof.

According to the third modification, the IC chip 213, the first bear chip 216, and the second bear chip 217 are simultaneously bent as shown by a dotted line in FIG. 28A at an interval for layering them.

Referring to FIG. 28B, the bent leads 272 are touched to the sensor substrates 206b and the image pick-up processing and control substrate 215b and are connected and are fixed by soldering. After connecting and fixing, unnecessary lead portions are cut off.

According to the third modification, referring to FIGS. 28A and 28B, upon accurately setting the bending interval, the sensor substrates 206b and the image pick-up processing and control substrate 215b maintain the predetermined interval therebetween by abutting the bent leads 272 against opposed pads on the inner-circumferential surface on both the sensor substrates 206b and the image pick-up processing and control substrate 215b. In this case, the interval is not limited to that in the case of setting the interval between the sensor substrates 206b and the image pick-up processing and control substrate 215b upon layering the IC chip 213, the first bear chip 216, and the second bear chip 217.

According to the third modification, similarly, since a plain electrical substrate can be used and the connecting member is integrally formed to the lead frame, the deviation of the substrates is prevented and the operability is improved. Further, the costs are reduced.

Seventh Embodiment

Next, a seventh embodiment of the present invention will be described with reference to FIGS. 29A to 31. FIG. 29A shows a plan view of a connecting member according to the seventh embodiment. FIG. 29B shows a side view of the connecting member.

According to the seventh embodiment, the connecting member corresponds to an MID (Molded Interconnect Devices) on which a plurality of connecting terminals are three-dimensionally formed. Generally, the MID is a device obtained by three-dimensionally forming a pattern onto an insulating molding member.

Referring to FIGS. 29A and 29B, according to the seventh embodiment, an MID 81 includes conductive portions 83. An MID main body 82 is formed with a substantially C shape which is obtained by notching, e.g., the down side of an insulating member such as a resin member. The conductive portions 83 are formed by a plurality of parallel patterns on the outer-circumferential surface portions on the upper, right, and left sides of the MID main body 82 in the height direction thereof. Further, the MID 81 includes an accommodating space portion 84 therein.

In this case, referring to FIG. 29B, a plurality of the conductive portions 83 are formed in parallel with the height direction so that they are vertical to the end surface shown in FIG. 29A (and the end surface on the down side). The conductive portion 83 is formed by plating a metal on the surface of a semi-cylindrical portion.

The outer shape of the MID 81 is formed with substantially the same as that of, e.g., a sensor substrate 206c (excluding the notched down-side portion).

Therefore, referring to FIG. 30, the IC chip 213 mounted on the rear surface of the sensor substrate 206c is accommodated in the accommodating space portion 84 by layering one end surface of the MID 81 onto the plain sensor substrate 206c. The first bear chip 216 and the second bear chip 217 mounted on the front surface of the plain image pick-up processing and control substrate are accommodated in the accommodating space portion 84 by layering the image pick-up processing and control substrate to another end surface of the MID 81.

The plain sensor substrate 206c shown in FIG. 30 includes conductive portions 85 having pads, which have the same shape as that of the conductive portion 83 shown in FIGS. 29A and 29B and which are formed near the upper, right, and left sides of the sensor substrate 206b. As shown in FIG. 30, the one end surface of the MID 81 is layered to the sensor substrate 206c, thereby touching the conductive portions 83 to the conductive portions 85 of the sensor substrate 206c. Therefore, the conductive portions 83 and 85 come into contact with each other adjacently in the height direction, and are easily connected and fixed by soldering.

Although not shown, the image pick-up processing and control substrate has the same conductive portions as those in the image pick-up processing and the control substrate 215c. Similarly, the image pick-up processing and control substrate is easily connected and fixed to the conductive portion 83 by soldering.

According to the seventh embodiment, the electrical substrate may be plain and the connecting terminal is integrally formed to the MID. Thus, the deviation of substrates is prevented and the operability is improved.

According to the first to seventh embodiments, the capsule endoscope is used as the capsule medical apparatus. However, a capsule medical apparatus 91 shown in FIG. 31 may be used for another medical action.

Figure 31:
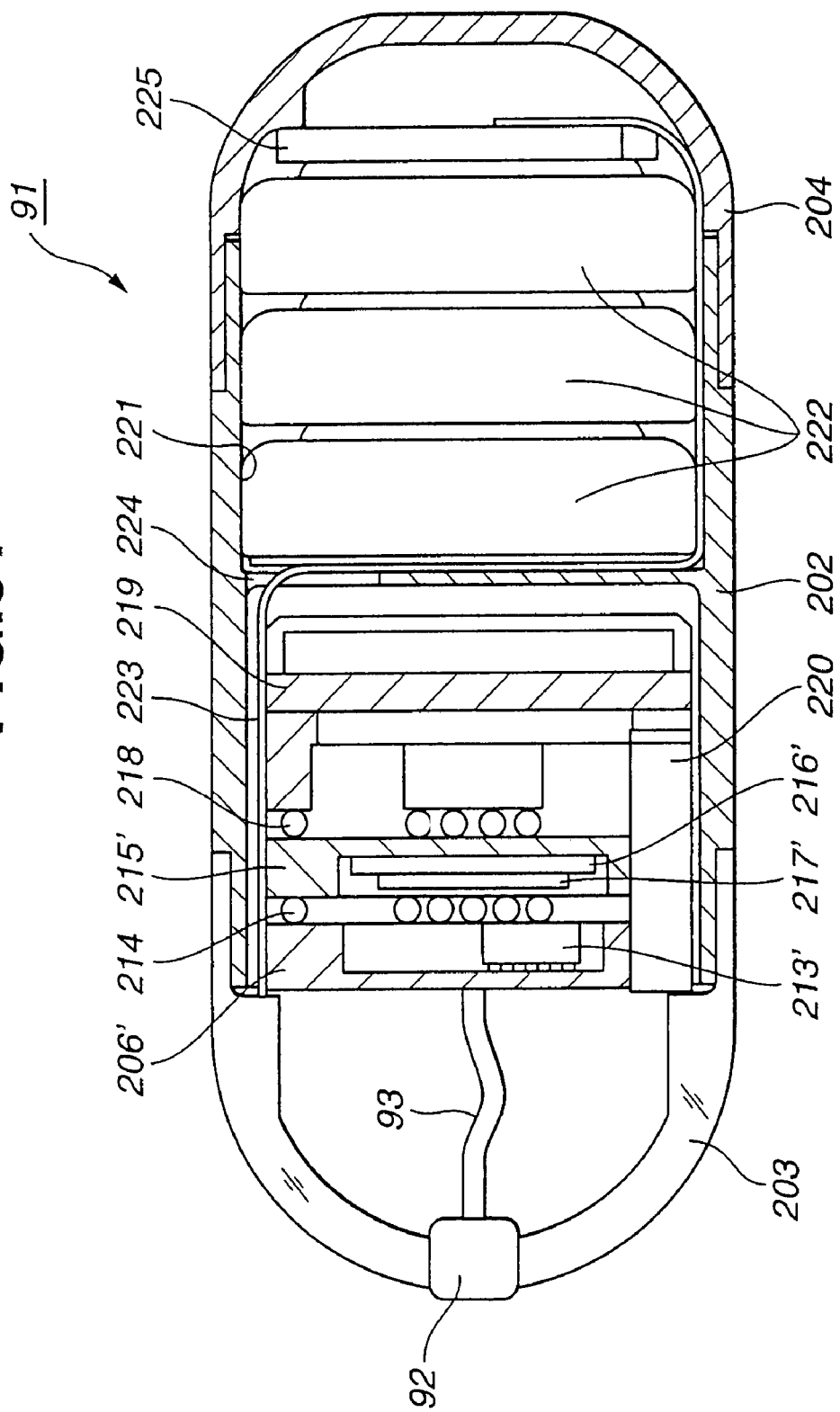

Referring to FIG. 31, the capsule medical device 91 detects pH in the body, and transmits, by radio, information on the detected pH to an extracorporeal unit arranged to the outside of the body.

Consequently, in the capsule medical device 91, a pH sensor 92 for measuring pH is attached to the distal end cover 203 in the capsule endoscope 201 shown in FIG. 16 to be exposed to the outer surface. An electrode in the distal end cover 203 is connected to a sensor substrate 206' via a signal line.

An IC chip 213' forming a driving circuit for driving the pH sensor 92 is mounted on the sensor substrate 206'. The sensor substrate 206' is connected and is fixed to a signal processing and control substrate 215' by the soldering balls 214. The signal processing and control substrate 215' has a cavity structure. A first bear chip 216' is flip-mounted on the signal processing and control substrate 215' for signal processing and control operation. Further, a second bear chip 217' is mounted on the top surface of the first bear chip 216' by wire bonding.

The signal processing and control substrate 215' is connected to the communication substrate 219 by the soldering balls 218. Other structures of the capsule medical device 91 shown in FIG. 31 are the same as those according to the fourth embodiment, the same reference numerals denote the same components, and a description thereof is omitted.

Functions for actual medical action of the capsule medical device 91 are different from those according to the fourth embodiment. However, advantages according to the seventh embodiment are the same as those according to the fourth embodiment.

Further, the capsule medical device according to the seventh embodiment can be applied to those having functions for other medical actions such as examination and treatment.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsule medical apparatus comprising:
a cylindrical capsule-shaped exterior casing of which at least one end portion is substantially hemispherical;
a plurality of electrical substrates with different functions, the electrical substrates being stored in the exterior casing and having an outer shape slightly smaller than an inner diameter of the exterior casing;
a connecting member comprising a plurality of soldering balls or a plurality of pins, the connecting member being electrically conductive and mechanically fixing the electrical substrates adjacent and opposed to one another, in a state where each of the plurality of electrical substrates are arranged in a direction orthogonal to a longitudinal direction of the exterior casing such that the electrical substrates are substantially parallel to one another;
a battery arranged in the exterior casing and adapted to supply power to the plurality of substrates; and
a flexible substrate, which is arranged in the exterior casing along a longitudinal direction of the exterior casing, which is provided with a power pattern which is electrically conductive with the battery and transmits power by the battery, and on which the power pattern is connected so as to be electrically conductive at end surfaces of the plurality of electrical substrates opposed to one another in the longitudinal direction of the exterior casing.

2. A capsule medical apparatus according to claim 1, wherein the plurality of soldering balls are used as the connecting member when no mounted parts are arranged between the adjacently opposed electrical substrates, and the plurality of pins are used as the connecting member when mounted parts are arranged between the adjacently opposed electrical substrates.

3. A capsule medical apparatus according to claim 1, wherein the connecting member further includes an MID (Molded Interconnect Devices) obtained by three-dimensionally forming thereon a plurality of connecting terminals or a lead frame formed integrally to a coupling portion which can easily be cut off after connection.

4. A capsule medical apparatus according to claim 1, wherein a pad, to which the connecting member of one electrical substrate is attached, is extended to the outer shape of the electrical substrate.

5. A capsule medical apparatus according to claim 1, wherein the plurality of electrical substrates are maintained to be positioned to one another, and the plurality of soldering balls between the plurality of electrical substrates are soldered by flowing them to a flow furnace in a lump.

6. A capsule medical apparatus according to claim 1, wherein the plurality of electrical substrates have a fitting hole for fitting the connecting member.

7. A capsule medical apparatus according to claim 1, wherein the connecting member comprises a plurality of soldering balls for electrically connecting the plurality of electrical substrates, and the inclination of the electric substrates can be prevented by connecting at least two sides of the plurality of electrical substrates.

8. A capsule medical apparatus according to claim 1, wherein the electrical substrates are substantially circular or substantially polygonal, and have substantially the same maximum outer shapes.

9. A capsule medical apparatus according to claim 1, wherein the plurality of electrical substrates has at least an image pick-up unit, a first electric substrate having a cave portion for fixing another electric part to the rear surface of the image pick-up unit, a second electric substrate having a cave portion for fixing a control portion for controlling at least the image pick-up unit, and a connecting terminal for connecting the first and second electric substrates.

10. A capsule medical apparatus according to claim 1, wherein two electric parts having different functions are layered and are mounted on one surface of at least one of the plurality of electric substrates.

11. A capsule medical apparatus according to claim 1, wherein an antenna for radio transmission is arranged substantially in parallel with an optical axis of an objective optical system arranged in the exterior casing.

12. A capsule medical apparatus according to claim 1, further comprising an illuminating unit and an image pick-up unit, wherein the illuminating unit comprises a plurality of light emitting diodes, light emitting timings of the plurality of light emitting diodes are controlled to be deviated within an exposure time of an image pick-up unit and to intermittently be lit on.

13. A capsule medical apparatus according to claim 1, further comprising an image pick-up unit arranged inside a hemispherical end portion in the exterior casing and an illuminating unit arranged in a circumference of the image pick-up unit, wherein the illuminating unit is supplied with power for illumination by the power pattern provided to the flexible substrate which is a separate body from the electrical substrates.

14. A capsule medical apparatus according to claim 1, wherein the flexible substrate is formed separately from the connecting member which is used for signal transmission, and wherein only the power pattern for transmitting power by the battery is formed on the flexible substrate.

* * * * *